US005475090A

United States Patent [19]
Granados et al.

[11] Patent Number: 5,475,090

[45] **Date of Patent: * Dec. 12, 1995**

[54] GENE CODED FOR A POLYPEPTIDE WHICH ENHANCES VIRUS INFECTION OF HOST INSECTS

[75] Inventors: Robert R. Granados, Ithaca, N.Y.; Yoshifumi Hashimoto, Kyoto, Japan

[73] Assignee: Boyce Thompson Institute for Plant Research, Ithaca, N.Y.

[ * ] Notice: The portion of the term of this patent subsequent to Nov. 27, 2007, has been disclaimed.

[21] Appl. No.: 971,624

[22] Filed: Nov. 4, 1992

Related U.S. Application Data

[63] Continuation-in-part of Ser. No. 663,560, Mar. 4, 1991, abandoned, which is a continuation-in-part of Ser. No. 313,226, Feb. 21, 1989, abandoned.

[51] Int. Cl.[6] .................................................. C07K 14/00

[52] U.S. Cl. ......................... 530/350; 424/405; 530/826; 530/387.1; 530/387.2; 530/387.3; 514/2; 514/12

[58] Field of Search ......................... 514/2, 12; 530/350, 530/387.1, 388.2, 388.3, 826; 424/405; 930/220

[56] References Cited

U.S. PATENT DOCUMENTS

| | | | |
|---|---|---|---|
| 4,904,645 | 2/1990 | Puritch | 514/65 |
| 4,973,667 | 11/1990 | Granados | 530/350 |
| 5,011,685 | 4/1991 | Granados | 424/93.6 |

OTHER PUBLICATIONS

Derksen, A. G. S. and Granados, R. R. *Virology* 167:242–250 (1988).
Peters, W. and Wiese, B. *J. Insect Physio.* 32:43–49 (1986).
Snyder, M., Sweatser, D., Young, R. A. and Davis, R. W. *Meth. Enzym.* 154:107–128 (1985).
Vlak, J. M. and Smith, G. E. *J. Virol.* 41:1118–1121 (1982).
Rohrmann, G. F. *J. Gen. Virol.* 67:1499–1513 (1986).
Tanada, Y. and Hukuhara, T. *J. Invertebr. Pathol.* 17:116–126 (1971).
Tanada, Y. and Hara, S. *Nature* 254:328–329 (1975).
Tanada, Y. *J. Insect Pathol.* 1:215–231 (1959).
Tanada, Y. Inoue, H., Hess, R. T., and Omi, E. M. *J. Inverebr. Pathol.* 35:249–255 (1980).
Tanada, Y. *J. Invertebr. Pathol.* 45:125–138 (1985).
Yamamoto, T., Kita, H. and Tanada, Y. *J. Gen. Virol.* 45:371–381 (1979).
Hamm, J. J. and Paschke, J. D. *J. Insect Pathol.* 5:187–197 (1963).
Whitlock, V. H. *J. Invertebr. Pathol.* 23:70–75 (1974).
Granados, R. R. and Williams, K. A. *The Biology of Baculoviruses*, CRC Press, Fla., vol. I:89–108 (1986).
Miller, L. K. *The Biology of Baculoviruses*, CRC Press, Fla., vol. I:217–238 (1986).
Dwyer, K. G. & Granados, R. R. *J. Virol.* 62:1535–1542 (1988).
Jacques R. P. *Can. Entomol.* 120:575–580 (1988).

Sears, M. K. et al. *J. Econ. Entomology* 76:368–374 (Apr. 1983).

Blake, M. S., Johnston, K. H., Russel–Jones, G. J. & Gotschlich, E. C. *Analytical Biochemistry* 136, 175–179.

Gallo, L. G., Corsaro, B. G., Hughes, P. R. & Granados, R. R. *Journal of Invertebrate Pathology* 58:203–210 (1991).
Goto, C. *Applied Entomology and Zoology* 25, 135–137 (1990).
Hashimoto, Y., Corsaro, B. G. & Granados, R. R. *Journal of General Virology* 72, 2645–2651 (1991).
Hara, S., Tanada, Y. & Omi, E. M. *Journal of Invertebrate Pathology* 27, 115–124 (1976).
Huber, M., Cabib, E. & Miller, L. H. *Proceedings of the National Academy of Sciences, U.S.A.* 88,2807–2810 (1991).
Hughes, P. R. & Wood, H. A. *Journal of Invertebrate Pathology* 37, 154–159 (1981).
Hughes, P. R., Wood, H. A., Burand, J. P. & Granados, R. R. *Journal of Invertebrate Pathology* 43, 343–350 (1984).
Hughes, P. R., van Beek, N. A. M. & Wood, H. A. *Journal of Invertebrate Pathology* 48, 187–192 (1986).
Laemmli, U. K. *Nature London* 227, 680–685 (1970).
Ooi, B. G., Rankin, C., & Miller, L. K. *Journal of Molecular Biology* 210, 721–736 (1989).
Rudzinska, M. A., Spielman, A., Lewngrub, S., Piesman, J. & Karakshian, S. *Cell and Tissue Research* 221, 471–481 (1982).
Sanger, F., Nicklen, S. & Coalson, A. R. *Proceedings of the National Academy of Sciences, U.S.A.* 74, 5463–5467 (1977).
Tanada, Y. & Hukuhara, T. *Journal of Invertebrate Pathology* 12, 262–268 (1968).
Tanada, Y. & Watanabe, H. *Journal of Invertebrate Pathology* 18, 307–312 (1971).
Tanada, Y., Himeno, M. & Omi, E. M. *Journal of Invertebrate Pathology* 21, 31–40 (1973).
Tanada, Y., Hess, R. T. & Omi, E. M. *Journal of Invertebrate Pathology* 26, 99–104 (1975).
Tanada, Y., Hess, R. T., Omi, E. M. & Yamamoto, T. *Microbios* 37, 87–93 (1983).
Towbin, H., Staehelin, R. & Gordon, J. *Proceedings of the National Academy of Sciences, U.S.A.* 76, 4350–4354.
Uchima, K., Harvey, J. P., Omi, E. M. & Tanada, Y. A. *Insect Biochemistry* 18, 645–650 (1988).
Vieira, J. & J. Messing. *Gene* 19, 259–286 (1982).
Yamamoto, T. & Tanada, Y. *Journal of Invertebrate Pathology* 32, 158–170 (1978).
Yamamoto, T. & Tanada. Y. *Virology* 107, 434–440 (1980).
Zhu, Y., Hukuhara, T. & Tamura, K. *Journal of Invertebrate Pathology* 54, 49–56 (1989).

*Primary Examiner*—Christopher S. F. Low
*Attorney, Agent, or Firm*—C. Harold Herr

[57] ABSTRACT

Cloning and sequencing certain baculovirus genes encoding polypeptides termed enhancins. The polypeptides are isolated from the occlusion body of certain baculoviruses such as *Trichoplusia ni* granulosis virus and *Pseudaletia unipuncta* granulosis virus, Hawaiian strain. The polypeptides have the ability of enhancing the infectivity of baculoviruses and are useful ingredients of pest control compositions.

8 Claims, 14 Drawing Sheets

```
CAGCGCGAAAACGGTTGGTGCCAATTACTGGTATATTGCTATGATCGAGTGACGTCATAA
GGGTCGATTCGCGACGGTCTCCCACGTGGCCTTCCATTGAGGTTTACGTGTTTGTGTATG    -315

CGTGCGAGTGTTTTTATAACCCAAAAACTCAGCCACACCGTGTCCACCGTACATATACTT
GTCCTTTTCCAATTCCACAATCCAAATTTCCGCAGAAACTCCTCCAATGTTGCACGATTT    -195

TTTTACAAGAGTCATTTTGCACGTTTACAAGAAATTTATTACAAGATTAGCTGCTTGTGA
TAAAGGTCTGCACGAGATGAGATTCAAATACGTAATGAGAATTGCGTGATTTGCACGAGT    -75

TTATATAGCATAATTTGCTAGGAATGTCTGTTGGTTTGTGATGTTTAGGTGTTCGCTGCA
TTAATTATAAGACTATGTCGTACAAGTGATTGTACCCGCTACCGTGCTACCGCCGTGGC    +46
              M  S  Y  K  V  I  V  P  A  T  V  V  P  P  W

TCAGAGTCGGTGAGAATTGGATATTCGCAAGACACAGACGCACCGAGGTGGGAGTCGTTC
 L  R  V  G  E  N  W  I  F  A  R  H  R  R  T  E  V  G  V  V
TACCGGCGAACACGAAATTTCGTGTACGAGCAGATTTCTCTAGGGCCGGCTTCACCCGAC    +166
 L  P  A  N  T  K  F  R  V  R  A  D  F  S  R  A  G  F  T  R

CCGTAATAGTGCGCCTCTTGAACAACAACCGTAGCACTGAACGAGAAATCAACTTGAACA
 P  V  I  V  R  L  L  N  N  N  R  S  T  E  R  E  I  N  L  N
                              1
ACGACCAATGGATGGAGGTGGAGCATGCGCACGAGAGTGTGCCTTTCGTAGATTGGCTGG    +286
 N  D  Q  W  M  E  V  E  H  A  H  E  S  V  P  F  V  D  W  L

TGGGCGAAAAGAACACTATGGCCGAAGTGTATTTTGAAATCGACGGACCACACATACCGC
 V  G  E  K  N  T  M  A  E  V  Y  F  E  I  D  G  P  H  I  P
TACCCGTGTACGTGTTCAACACGAGACCCGTCGAACACTTTAAGAGCGAGTATCGCCAAA    +406
 L  P  V  Y  V  F  N  T  R  P  V  E  H  F  K  S  E  Y  R  Q

GTTCGTCTGGCTACTGCTTTCTATATTTGGACCTGGTCTGTATGTTGGTACCGCCCGCTA
 S  S  S  G  Y  C  F  L  Y  L  D  L  V  C  M  L  V  P  P  A
GCAAAAACGCTTTATTGGACGTGAACATTTTCGAGCTTCATCAATTTTATAACGAAATCA    +526
 S  K  N  A  L  L  D  V  N  I  F  E  L  H  Q  F  Y  N  E  I

TTAATTACTATGATGACCTGTGCGGCTTGGTCGAGGATCCATACGCAGACACTGTCGATT
 I  N  Y  Y  D  D  L  C  G  L  V  E  D  P  Y  A  D  T  V  D
CGAATTTACCCAACAAGGCTGCTTTCGTGAAAGCTGATGCTGGCGGTCCGGGTGGTGCGT    +646
 S  N  L  P  N  K  A  A  F  V  K  A  D  A  G  G  P  G  G  A

ATTATGGACCATTTTGGACGGCACCGGCGAGCTCAAACCTTGGTGATTACCTCAGAATAT
 Y  Y  G  P  F  W  T  A  P  A  S  S  N  L  G  D  Y  L  R  I
CGCCGACCAACTGGATGGTAATTCACGAGCTGGGTCATGCATACGATTTTGTGTTTACCG    +766
 S  P  T  N  W  M  V  I  H  E  L  G  H  A  Y  D  F  V  F  T

TCAACACTATACTCATTGAAATTTGGAACAACTCTTTATGCGATCGCATCCAATACAAGT
 V  N  T  I  L  I  E  I  W  N  N  S  L  C  D  R  I  Q  Y  K
                              2
GGATGAACAAAATTAAAAGACAACAACTGGCTCGCGTCTATGAAAATAGACGACCGCAGA    +886
 W  M  N  K  I  K  R  Q  Q  L  A  R  V  Y  E  N  R  R  P  Q

AAGAGGCGACCATTCAGGCGCTGATCGACAATAACAGCCCGTTCGATAATTGGGGCTTTT
 K  E  A  T  I  Q  A  L  I  D  N  N  S  P  F  D  N  W  G  F
                              3
TTGAGAGGCTGATAATATTCACGTGGCTGTACAACCCGCAAAGAGGACTAGACACATTGC    +1006
 F  E  R  L  I  I  F  T  W  L  Y  N  P  Q  R  G  L  D  T  L

GTAACATCAACCATTCGTACAGGGTGCACGCCACCCGCAACTCTTCTATACCGTACCCGC
 R  N  I  N  H  S  Y  R  V  H  A  T  R  N  S  S  I  P  Y  P
          4                              5
AAATATGGTCATGGCTAACGACTTCTGCTTACGACAACTTTTGGTTATATTTTAATTTGG    +1126
 Q  I  W  S  W  L  T  T  S  A  Y  D  N  F  W  L  Y  F  N  L

TAGGCGTGTACCCGGCAGACTTTTACGTAAACGAACACAACAAAGTTGTTCATTTCAATC
 V  G  V  Y  P  A  D  F  Y  V  N  E  H  N  K  V  V  H  F  N
TACACTTGAGAGCTTTGGCGTTGGGGCAGAGTGTGCGTTATCCCATTAAATATATAATTA    +1246
 L  H  L  R  A  L  A  L  G  Q  S  V  R  Y  P  I  K  Y  I  I
```

FIG.3A

```
CAGACTTTGATCTGGTGAGCAAAAACTACGACATTAAACAGTATTTAGAGAGTAATTTCG
 T  D  F  D  L  V  S  K  N  Y  D  I  K  Q  Y  L  E  S  N  F
ATCTGGTTATACCAGAAGAATTGCGGCAGACCGATTTGTTGGCGGACGTGAGGGTGGTTT   +1366
 D  L  V  I  P  E  E  L  R  Q  T  D  L  L  A  D  V  R  V  V

GTGTGATTGACGATCCGTCGCAGATTGTGGGCGAACCGTTTAGCGTGTACGACGGGAACG
 C  V  I  D  D  P  S  Q  I  V  G  E  P  F  S  V  Y  D  G  N
AGCGAGTGTTCGAGAGTACGGTGGCCACGGACGGAAACATGTATCTGGTGGGCGTGGGTC   +1486
 E  R  V  F  E  S  T  V  A  T  D  G  N  M  Y  L  V  G  V  G

CGGGAGTGTACACGTTGCGTGCGCCACGCGGCAAAAACAAACGCTACAAACTCCATTTGG
 P  G  V  Y  T  L  R  A  P  R  G  K  N  K  R  Y  K  L  H  L
CACATTCGCCCAGAGAGCCCGTTCATCCGGCCAACGACCACATGTATCTGCTCGTGACGT   +1606
 A  H  S  P  R  E  P  V  H  P  A  N  D  H  M  Y  L  L  V  T

ATCCCTACTACAATCAAACGTTGACATACACACCGTACGTAAATTCTGACCTAGCCGTCG
 Y  P  Y  Y  Y  N  Q  T  L  T  Y  T  P  Y  V  N  S  D  L  A  V
            ‾‾‾‾‾‾‾
               6
ACATGGCTCATTTGTTCGGCAGCAACGATCGTAGGTATGTAGCCACGATATATTTCAATC   +1726
 D  M  A  H  L  F  G  S  N  D  R  R  Y  V  A  T  I  Y  F  N

CATTCGAACAAACAGTCACCGTACATCTAAACAATATTCGTGCCGGTCGTGAAAACAACA
 P  F  E  Q  T  V  T  V  H  L  N  N  I  R  A  G  R  E  N  N
                                                          ‾‾‾
                                                           7
CTACCCTGTACTTTGAAATGGTAATTAGCAACCCGTTCAACGGGCAGAGCCAAACTTTCA   +1846
 T  T  L  Y  F  E  M  V  I  S  N  P  F  N  G  Q  S  Q  T  F
 ‾‾
  8
CTATACTCGAAGACAATCCCACTTTACGACAAGGCTACTACAAATTTGACGTGGTCACGT
 T  I  L  E  D  N  P  T  L  R  Q  G  Y  Y  K  F  D  V  V  T
            ‾‾‾‾‾‾‾
               9
ACAGCTCCATAAGGCTGAATATGAGCGTCGCGGGTCGGCTATTATTTCGGCGATACATTT   +1966
 Y  S  S  I  R  L  N  M  S  V  A  G  R  L  L  F  R  R  Y  I
                  ‾‾‾‾‾‾‾
                    10
TTGCCGGAGGTACCACCACGCTGACCATGTTCCCAAATCAAGTACTTGAGCCCAATTTGT
 F  A  G  G  T  T  T  L  T  M  F  P  N  Q  V  L  E  P  N  L
TTCCAGACGGTTCCGCCTTGAATAGGACATTGGCACGACTAAGAGAACAGGCCGCCTTCC   +2086
 F  P  D  G  S  A  L  N  R  T  L  A  R  L  R  E  Q  A  A  F
                     ‾‾‾‾‾‾‾
                        11
TAGATAATTATTCACAACTTATGTATATTGAAAACGAGTTGCGCGACACGATTTATTTGG
 L  D  N  Y  S  Q  L  M  Y  I  E  N  E  L  R  D  T  I  Y  L
     ‾‾‾‾‾‾‾
        12
CCTCCCAGTTGGTAGATCCTGCGTCAGACGAATTTGTAAAGTATTATCCAGACTACTTCA   +2206
 A  S  Q  L  V  D  P  A  S  D  E  F  V  K  Y  Y  P  D  Y  F

GAGATCCGCACACGTACGTGTACTTGTTTCGTTTCAGAGGTCTGGGTGATTTCGTGTTAT
 R  D  P  H  T  Y  V  V  Y  L  F  R  F  R  G  L  G  D  F  V  L
TAGACTTGCAGATTGTACCATTGCTAAATTTGGCCACTGTACGTATAGCCAACATCCAAA   +2326
 L  D  L  Q  I  V  P  L  L  N  L  A  T  V  R  I  A  N  I  Q

ACGGTCCCCACTCGTACTTCGATACTTTGTATTTTAAAGTGGAGTTGCGCGACACAAACG
 N  G  P  H  S  Y  F  D  T  L  Y  F  K  V  E  L  R  D  T  N
GTGCGATTGTGTTTTCGTATTCGCGCCGTGGCAACGAGCCGATGACACCCGAACACCATA   +2446
 G  A  I  V  F  S  Y  S  R  R  G  N  E  P  M  T  P  E  H  H

AATTTGAAGTGTACAGTGGTTACACCGTAGAATTGTTCATGCGGGAACCCGGTAATCGAT
 K  F  E  V  Y  S  G  Y  T  V  E  L  F  M  R  E  P  G  N  R
TACAATTGATTGTGAACAAAATGCTTGACACAGCGTTGCCGTCTACTCAAAACATTTTCG   +2566
 L  Q  L  I  V  N  K  M  L  D  T  A  L  P  S  T  Q  N  I  F

CTCGCATCACCGACACTCAATTAGTGGTGGGGGATACGAGCATTGAAGATAACCTTGTAA
 A  R  I  T  D  T  Q  L  V  V  G  D  T  S  I  E  D  N  L  V
CGAGTATTAATGTAGATTGTGGCGACGACGACAACCAAAAGATAAGAGTTGTGGAAACGT   +2686
 T  S  I  N  V  D  C  G  D  D  D  N  Q  K  I  R  V  V  E  T

TAAAAATGATAGCGTTCTAATAACGTTCAACAGTCAGTTATCGACTGTCGCCGCGACGAC
 L  K  M  I  A  F  -  -
ATGACACTGGTGGGTGTAGTAGTTTGCGTGCTGTTGTTATCGTCTGTAGACGGTTATTCG   +2806
```

FIG.3B

```
TTTTATTCGTCGATTGAAGCCCTGCTTTTGAACGATCGCACACAACTTTGCATAGGCGAC
TGTTACGAACGCAATGGCCAGCATTTGTGTGCCAGCACGTGGTCGGGATCAGAGTCTCGG   +2926

TGCATAAGTGTTTTCAACAAGACCAAACACTATCGTACGGAGACTAACGGAAAATGCATA
AGTAACTGTGCCAACTTCAACAACTACGCCCACGAATGGTGTGCCGTGTCCCGGTCGAAA   +3046

TGGGGCCGTTGCAGCAGACGACTGGCGCTCACAGCGACACGAACACACGCCACCCACAAC
AAGTTCAAGACATGTG                                                +3122
```

FIG.3C

```
PuGv-H - ATAAGACTATGTCGTACAAAGTGATTGTACCCGCTACCGTGCTACCGCCGTGGCTCAGAG
TnGV   - ------------------------------------------------------------
         TCGGTGAGAATTGGATATTCGCAAGACACAGACGCACCGAGGTGGGAGTCGTTCTACCGG +120
         ------------------------------------------------------------

PuGV-H - CGAACACGAAATTTCGTGTACGAGCAGATTTCTCTAGGGCGGGCTTCACCCGACCCGTAA
TnGV   - ----------------------------------------C-------------------
         TAGTGCGCCTCTTGAACAACAACCGTAATACTGAACGAGAAATCAACTTGAACAACGACC +240
         ---------------------------GC-------------------------------

PuGV-H - AATGGATGGAGGTGGAGCATGCGCACGAGAGTGTGCCGTTTGTCGATTGGCCGGTGGGCG
TnGV   - -------------------------------------T--C--A-------T--------
         AAAGGAACATTATGGCCGAAGTGTATTTTGAAATCGACGGACCACACATACCGCTGCCCG +360
         ---A-----C----------------------------------------------A---

PuGV-H - TGTACGTGTTCAACACGAGACCTGTCGAACACTTTAAGAGCGAGTATCGCCAAAGTTCGT
TnGV   - ----------------------C-------------------------------------
         CTGGCTACTGCTTTCTATATTTGGACCTGGTCTGTATGTTGGTACCGCCCGCTAGCAAAA +480
         ------------------------------------------------------------

PuGV-H - ACGCTTTATTGGACGTGAACATTTTCGAGCTTCATCAATTTTATAACGAAATCATTAATT
TnGV   - ------------------------------------------------------------
         ACTATGATGACCTGTGCGGCTTGGTCGAGGATCCATACGCAGACACTGTCGATTCGAATT +600
         ------------------------------------------------------------

PuGV-H - TACCCAACAAGGCTGCTTTCGTGAAAGCTGATGCTGGCGGTCCGGGTGGTGCGTATTATG
TnFV   - ------------------------------------------------------------
         GACCATTTTGGACGGCACCGGCGAGCTCAAACCTTGGTGATTACCTCAGAATATCGCCGA +720
         ------------------------------------------------------------

PuGV-H - CCAACTGGATGGTAATTCACGAGCTGGGTCATGCATACGATTTTGTGTTTACCGTCAACA
TnGV   - ------------------------------------------------------------
         CTATACTCATTGAAATTTGGAACAACTCTTTATGCGATCGCATCCAATACAAGTGGATGA +840
         ------------------------------------------------------------

PuGV-H - ACAAAACCAAAAGACAACAACTGGCTCGCGTCTATGAAAATAGACGACCGCAGAAAGAGG
TnGV   - ------TT----------------------------------------------------
         CGACCATTCAGGCGCTGATCGACAATAACAGCCCGTTCGATAATTGGGGCTTTTTTGAGA +960
         ------------------------------------------------------------

PuGV-H - GGCTGATAATATTCACGTGGCTGTACAACCCGCAAAGAGGACTAGACACATTGCGTAACA
TnGV   - ------------------------------------------------------------
         TCAACCATTCGTACAGGGTGCACGCCACCCGCAACTCTTCTATACCGTACCCGCAAATAT +1080
         ------------------------------------------------------------

PuGV-H - GGTCATGGCTAACGACTTCTGCTTACGACAACTTTTGGTTATATTTTAATTTGGTAGGCG
TnGV   - ------------------------------------------------------------
         TGTACCCGGCAGACTTTTACGTAAACGAACACAACAAAGTTGTTCATTTCAATCTACACT +1200
         ------------------------------------------------------------

PuGV-H - TGAGAGCTCTGGCGTTGGGGCAGAGTGTGCGTTATCCCATTAAATATATAATTACAGACT
TnGV   - --------T---------------------------------------------------
         TTGATCTGGTGAGCAAAAACTACGACATTAAACAGTATTTAGAGAGTAATTTCGATCTGG +1320
         ------------------------------------------------------------

PuGV-H - TTATACCAGAAGAATTGCGGCAGACCGATTTGTTGGCGGACGTGAGGGTGGTTTGTGTGA
TnGV   - ------------------------------------------------------------
         TTGACGATCCGTCGCAGATTGTGGGCGAACCGTTTAGCGTGTACGACGGGAACGAGCGAG +1440
         ------------------------------------------------------------
```

FIG.6A

```
PuGV-H   TGTTCGAGAGTACGGTGGCCACGGACGGAAACATGTATCTGGTGGGCGTGGGTCCGGGAG
TnGV     ------------------------------------------------------------
         TGTACACGTTGCGTGCGCCACGCGGCAAAAACAAACGCTACAAACTCCATTTGGCACATT  +1560
         ------------------------------------------------------------

PuGV-H   CGCCCAGAGAGCCCGTTCATCCGGCCAACGACCACATGTATCTGCTCGTGACGTATCCCT
TnGV     ------------------------------------------------------------
         ACTACAATCAAACGTTGACATACACACCGTACGTAAATTCTGACCTAGCCGTCGACATGG  +1680
         ------------------------------------------------------------

PuGV-H   CTCATTTGTTCGGCAGCAACGATCGTAGGTATGTAGCCACGATATATTTCAATCCATTCG
TnGV     ------------------------------------------------------------
         AACAAACAGTCACCGTACATCTAAACAATATTCGTGCCGGTCGTGAAAACAACACTACCC  +1800
         ------------------------------------------------------------

PuGV-H   TGTACTTTGAAATGGTAATTAGCAACCCGTTCAACGGGCAGAGCCAAACTTTCACTATAC
TnGV     ------------------------------------------------------------
         TCGAAGACAATCCCACTTTACGACAAGGCTACTACAAATTTGACGTGGTCACGTACAGCT  +1920
         ------------------------------------------------------------

PuGV-H   CCATAAGGCTGAATATGAGCGTCGCGGGTCGGCTATTATTT GGCGATACATTTTTGCCG
TnGV     ---------------------------------------C--------------------
         GAGGGTACCACCACGCTGACCATGTTCCCAAATCAAGTACTTGAGCCCAATTTGTTTCCA  +2039
         ------------------------------------------------------------

PuGV-H   GACGGTTCCGCCTTGAATAGGACATTGGCACGACTAAGAGAACAGGCCGCCTTCCTAGAT
TnGV     ------------------------------------------------------------
         AATTATTCACAGCTTATGTATATTGAAAACGAGTTGCGCGACAGCATTTATTTGGCCTCC  +2159
         -----------A-------------------------CG---------------------

PuGV-H   CAGTTGGTAGATCCTGCGTCAGACGAATTTGTAAAGTATTATCCAGACTACTTCAGAGAT
TnGV     ------------------------------------------------------------
         CCGCACACGTACGTGTACTTGTTTCGTTTTAGAGGTCTGGGTGATTTTGTGTTATTAGAC  +2279
         ----------------C-----------------C-------------------------

PuGV-H   TTGCAGATTGTACCATTGCTAAATTTGGCAACTGTACGTATAGCTAACAACCACAACGGT
TnGV     ----------------C-----------------C----T---A----------------
         CCCCACTCGTACTTCGATACTTTGTATTTTAAAGTGGAGTTGCGCGACACAAACGGTGCG  +2399
         ------------------------------------------------------------

PuGV-H   ATTGTGTTTTCGTATTCGCGCCGTGGCAACGAGCCGATGACACCCGAACACCATAAATTT
TnGV     ------------------------------------------------------------
         GAAGTGTACAGTGGTTACACCGTAGAATTGTTCATGCGGGAACCCGGTAATCGATTACAA  +2519
         ------------------------------------------------------------

PuGV-H   TTGATTGTGAACAAAATGCTTGACACAGCGTTGCCGTCTACTCAAAACATTTTCGCTCGC
TnGV     ------------------------------------------------------------
         ATCACCGACACTCAATTAGTGGTGGGGGATACGAGCATTGAAGATAACCTTGTAACGAGT  +2639
         ------------------------------------------------------------

PuGV-H   ATTAATGTAGATTGTGGCGACGACGACAACCAAAAGATAAGAGTTGTGGAAACGTTAAAA
TnGV     ------------------------------------------------------------
         ATGATAGCGTTCTAATAACGTTCAACAGTCAGTTATCGACTGTCGCCGCGACGACATGAC  +2759
         ------------------------------------------------------------

PuGV-H   ATGGTGGGTGTAGTAGTTTGCGTGCTGTTGTTATCGTCTGTACACGGTTATTCGTTTTAT
TnGV     ----------------------------------G-------------------------
         TCGTCGATTGAAGCCCTGCTTTTGAACGATCGCACACAACTTTGCATAG             +2868
         ------------------------------------------------------------
```

FIG.6B

PuGV-H - MSYKVIVPATVVPPWLRVGENWIFARHRRTEVGVVLPANTKFRVRADFSRAGFTRPVIVR -60
TnGV   - ------------------------------------------------------------

PuGV-H - LLNNNRNTEREINLNNDQWMEVEHAHESVPFVDWPVGERNIMAEVYFEIDGPHIPLPVYV -120
TnGV   - ------S---------------------L---K-T-------------------------

PuGV-H - FNTRPVEHFKSEYRQSSSGYCFLYLDLVCMLVPPASKNALLDVNIFELHQFYNEIINYYD -180
TnGV   - ------------------------------------------------------------

PuGV-H - DLCGLVEDPYADTVDSNLPNKAAFVKADAGGPGGAYYGPFWTAPASSNLGDYLRISPTNW -240
TnGV   - ------------------------------------------------------------

PuGV-H - MVIHELGHAYDFVFTVNTILIEIWNNSLCDRIQYKWMNKTKRQQLARVYENRRPQKEATI -300
TnGV   - ---------------------------------I--------------------------

PuGV-H - QALIDNNSPFDNWGFFERLIIFTWLYNPQRGLDTLRNINHSYRVHATRNSSIPYPQIWSW -360
TnGV   - ------------------------------------------------------------

PuGV-H - LTTSAYDNFWLYFNLVGVYPADFYVNEHNKVVHFNLHLRALALGQSVRYPIKYIITDFDL -420
TnGV   - ------------------------------------------------------------

PuGV-H - VSKNYDIKQYLESNFDLVIPEELRQTDLLADVRVVCVIDDPSQIVGEPFSVYDGNERVFE -480
TnGV   - ------------------------------------------------------------

PuGV-H - STVATDGNMYLVGVGPGVYTLRAPRGKNKRYKLHLAHSPREPVHPANDHMYLLVTYPYYN -540
TnGV   - ------------------------------------------------------------

PuGV-H - QTLTYTPYVNSDLAVDMAHLFGSNDRRYVATIYFNPFEQTVTVHLNNIRAGRENNTTLYF -600
TnGV   - ------------------------------------------------------------

PuGV-H - EMVISNPFNGQSQTFTILEDNPTLRQGYYKFDVVTYSSIRLNMSVAGRLLFGDTFLPEGT -660
TnGV   - ---------------------------------------------------RRYIFAG--

PuGV-H - TTLTMFPNQVLEPNLFPDGSALNRTLARLREQAAFLDNYSQLMYIENELRDSIYLASQLV -720
TnGV   - -----------------------------------------------T------------

PuGV-H - DPASDEFVKYYPDYFRDPHTYVYLFRFRGLGDFVLLDLQIVPLLNLATVRIANNHNGPHS -780
TnGV   - ------------------------------------------------------IQ----

PuGV-H - YFDTLYFKVELRDTNGAIVFSYSRRGNEPMTPEHHKFEVYSGYTVELFMREPGNRLQLIV -840
TnGV   - ------------------------------------------------------------

PuGV-H - NKMLDTALPSTQNIFARITDTQLVVGDTSIEDNLVTSINVDCGDDDNQKIRVVETLKMIA -900
TnGV   - ------------------------------------------------------------

PuGV-H - FZ -902
TnGV   - --

FIG.7

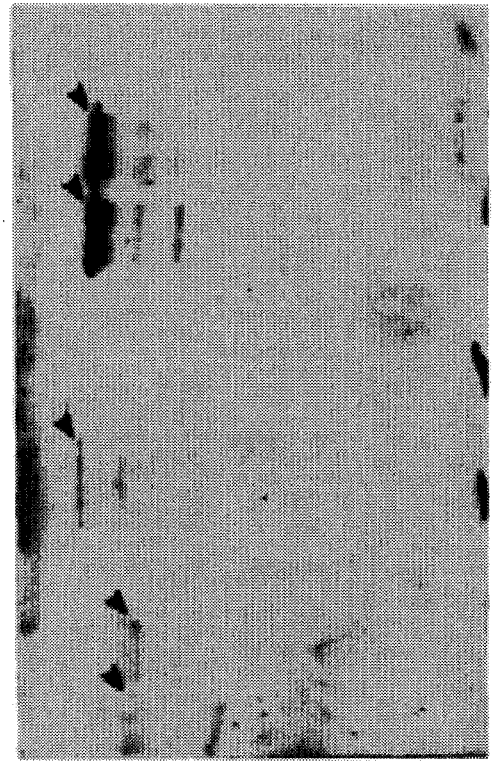
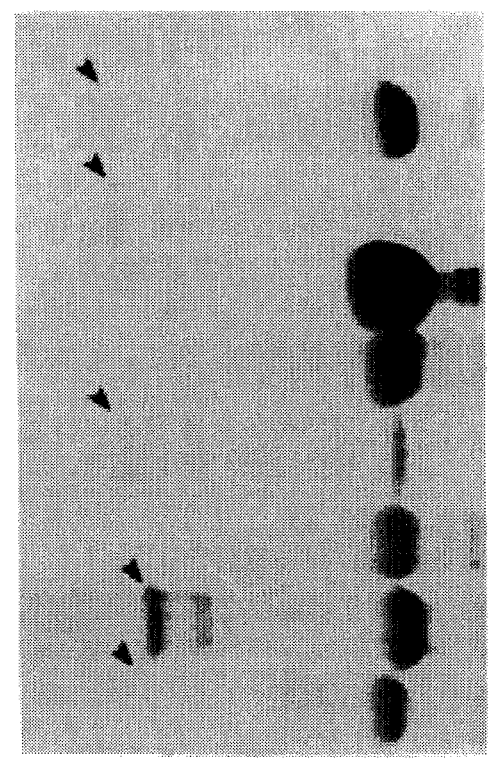
FIG. 10b
FIG. 10a

GENE CODED FOR A POLYPEPTIDE WHICH ENHANCES VIRUS INFECTION OF HOST INSECTS

Cross-Reference to Related Applications. This is a continuation-in-part application of our application Ser. No. 07/663,560 filed Mar. 4, 1991, which in turn is a continuation-in-part application Ser. No. 07/313,226 filed Feb. 21, 1989, both now abandoned.

BACKGROUND OF THE INVENTION

The invention relates to the cloning and sequencing of novel viral genes from certain baculoviruses for insect control. More particularly, the invention relates to an isolated and cloned DNA from a granulosis virus which comprises an amino acid sequence of the viral gene encoding a polypeptide isolated from occlusion bodies of certain baculoviruses and which polypeptide possesses the biological activity of enhancing baculovirus infectivity. This invention also relates to isolated and purified baculovirus proteins which are characterized by enhancing the infectivity of baculoviruses. Such proteins termed herein as "enhancins" are found within the viral occlusion body, have a disruptive effect on the insect peritrophic membrane (PM) proteins, and/or interact with the midgut epithelium in such a manner as to permit the increased adsorption, penetration and uptake of virus particles by midgut cells with a concomitant increase in host mortality.

The publications used to illuminate the background of the invention, and in particular cases, to provide additional details respecting its practice are incorporated herein by reference, and for convenience, are numerically referenced by the following text and respectively grouped in the appended bibliography. Copies of all of the references mentioned in this bibliography are attached to the INFORMATION DISCLOSURE STATEMENT filed concurrently herewith.

FIELD OF THE INVENTION

Present in the protein occlusion bodies (OBs) of some baculoviruses is a unique viral-encoded protein which enhances viral infection of the host insect. This protein is referred to herein as the virus enhancing factor (VEF) and/or as the synergistic factor (SF). Pest control compositions comprising this factor and nuclear polyhedrosis viruses are the subject matter of U.S. Pat. Nos. 4,973,667, 5,011,685.

Studies on the mode of action of the VEF isolated from *Trichoplusia ni* (cabbage looper) granulosis virus (TnGV) showed that the VEF caused rapid degradation of the peritrophic membrane which lines the midgut lumen of lepidopterous larvae. Larval bioassays suggested that this alteration made the peritrophic membrane more permeable to invading baculoviruses resulting in at least a 25-fold increase in larval mortality (1,2).

DESCRIPTION OF RELATED ART

Closely related to, or identical with, the VEF protein is a lipoprotein, originally isolated in crude form from a Hawaiian strain of *Pseudaletia unipuncta* granulosis virus (PuGV-H), but not cloned or sequenced. It is described by Tanada and co-workers (7, 8, 10) as the "synergistic factor" (SF) and as having a calculated molecular weight between 90K and 160K (6, 24, 35, 42 and 43). The SF was released from the capsule upon dissolution in the midgut, and was the localized to the microvillar surface of the midgut cell membrane (9,37) where it caused an apparent increase in the uptake of enveloped nucleocapsids (36). The binding of SF to the midgut membrane was found to be specific with a calculated equilibrium constant of $1.57 \times 10^{-9}$M (39).

It has been postulated by Hashimoto et al (23) that the two proteins (VEF and SF) are closely related and have similar dual modes-of-action: peritrophic membrane disruption and increased virus uptake. Evidence to support this relationship comes from southern hybridizations of PuGV-H genomic DNA with the VEF gene and western blots of dissolved PuGV-H occlusion bodies with an anti-VEF polyclonal antiserum (23). Tanada determined that this SF in the capsule of PuGV-H increased the larval susceptibility to *P. unipuncta* nuclear polyhedrosis virus (PuNPV) (8).

Since viral enhancing proteins are important at early stages of host infection, it is important to identify and locate the position of the VEF gene and the SF gene on the viral genome. A need, therefore, exists to clone and sequence both the VEF gene of TnGV and the SF gene of PuGV-H. It is an object of this invention to satisfy such a need. Another object is to compare the SF and TnGV VEF genes by showing their extremely high degree of sequence similarity and by demonstrating their similar affects on *T. ni* PMs and AcMNPV infections in *T. ni* larvae. Still another object is to show sequence homology and/or serological relatedness of the virulence genes and/or enhancing proteins among different baculoviruses.

SUMMARY OF THE INVENTION

The above-mentioned objects of the present invention, which will hereinafter become more readily apparent from the following description, have been attained by first isolating and purifying the VEF gene, which comprises a DNA molecule encoding a polypeptide of molecular weight 104 Kd and is found in the granulin fraction of TnGV OBs purified by SEPHACRYL® S-200 SUPERFINE, a general purpose gel filtration medium with a wet bead diameter of 40–105 μm prepared by covalently cross-linking allyl dextran with N,N¹-methylene bisacrylamide to give a rigid gel with a carefully controlled range of pore sizes, (2.6×34 cm) column, possessing a biological activity and wherein said polypeptide has a total of 901 amino acid residues in the amino acid sequence of the polypeptide. Besides cloning and sequencing the gene encoding the viral enhancing factor (VEF) of TnGv, applicants have also successfully isolated the SF gene and determined its complete nucleotide sequence.

The gene encoding for the viral enhancing factor (VEF) of TnGv has been cloned from a lambda gtll expression library, and the complete nucleotide sequence determined. The VEF gene encodes a protein with a predicted molecular weight of 104 Kd which does not share homology to any previously reported proteins. The apparent promotor is located 4 bp upstream of the initiation codon and represents a consensus baculovirus late promoter (ATAAG). This has been confirmed by the identification of VEF mRNA in northern blots of infected larvae at 6 days but not 3 days post infection. Three repeats of the sequence 'TTACAAGA' which match the baculovirus late promoter in 4 of 5 nucleotide have been identified between 149 and 192 bp upstream of the initiation codon. While the function of these sequences is unknown, they are not believed to be transcriptionally active since they diverge from the consensus promoter at the invariant 'T' position. Using the VEF gene as a probe in southern blots of genomic DNAs, homologous sequences have been identified in PuGV-H and *Heliothis armigera* GV (HaGV) but not *Erinnyis ello* GV, (EeGV), *Autographa californica* nuclear polyhedrosis virus (AcMNPV) or *Trichoplusia ni* nuclear polyhedrosis virus (TnSNPV). In addition, SDS-PAGE analysis of dissolved viral occlusion bodies have demonstrated proteins with a molecular weight similar to VEF in PuGV-H and HaGV.

As pointed out above, the gene encoding the synergistic factor (SF) of PuGV-H has been cloned by applicants and the complete nucleotide sequence determined. The SF gene encodes a protein with a predicted molecular weight of 104 Kd which shares a 99.1% and 98.2% homology with the nucleotide and amino acid sequence of the viral enhancing factor (VEF) gene of TnGv, respectively. A majority of the differences in the amino acid sequences of the two viruses result from two reciprocal frameshifts which occur between nucleotide +1962 and +1985 of the SF gene. Both enhancing proteins have similar activity in neonate larvae of *T. ni* (2.4 fold enhancement) and in vitro peritrophic membrane assays. Using a polyclonal antibody directed against TnGV VEF, 17 baculoviruses were screened by western blot hybridization. Cross reactive proteins are found in seven GVs isolated from 4 families of Lepidoptera. These putative enhancing proteins can be separated into 3 groups based on size: HaGV (110 Kd); PuGV-H, *Pieris rapae* GV (PrGV), *Scotogramma trifolii* GV (StGV), and TnGV (104 Kd); and *Cydia pomonella* GV (CpGV) and *Estigmene acrea* GV (80 Kd). The name "enhancin" has been proposed for these enhancing proteins.

DESCRIPTION OF THE DRAWINGS

A more complete appreciation of the invention and the attendant advantages thereof will be readily attained as the same becomes better understood by reference to the following details of description when considered in connection with the accompanying drawings, i.e. FIGS. 1–11.

FIG. 1. Mapping of the VEF gene of TnGV. a) a Hind III restriction map of the TnGV genome. By convention, the smallest fragment containing all of the granulin gene is assigned to be the first fragment at the left of the linearized map. A fine map of the b) Hind III-M fragment of TnGV and c) fusion gene of lambda F. The striped box indicates the position of the VEF gene while the open box indicates non-coding TnGV sequences inserted into the lambda gtll. The entire insert in lambda F is demarcated by the asterisks. The size of the DNA is indicated by scale, and the restriction sites for BamHI(B), ClaI(C), EcoRI(E), HindIII(H), KpnI(K), and SalI(S) are indicated.

FIG. 2. Western bolt analysis of lambda lysogens from lambda F (lane 1 or lambda gtll (lane 2) probed with either anti-VEF polyclonal antibody (lane 1) or an anti-β-galactosidase monoclonal antibody (lane 2). Lysogens were first separated on a 10% SDS-PAGE gel and then electrophoretically transferred to nitrocellulose. The 153 Kd protein identified by the anti-VEF polyclonal antibody consists of 39 Kd VEF carboxy-terminal and 114 Kd of β-galactosidase.

FIG. 3. The nucleotide sequence of the VEF gene from TnGV. The gene has been translated using the single-letter amino acid code. The bolded sequence represents the consensus baculovirus late promoter (5), and the underlined sequences represents 3 repeats of the sequence (TTACAAGA) which matches the promoter in 4 of the 5 base pairs. Double underlined sequences indicate possible glycosylation sites. The DNA sequence of a 3.5 Kb portion of Hind III-M fragment was determined by dideoxy chain termination method using bacteriophage T7 DNA polymerase. Sequence data were compiled and analyzed using the software program of PCGENE. In this sequence, A stands for deoxyadenyl, G for deoxyguanyl, C deoxycytidyl, and T is thymidyl. The amino acids encoded by the above DNA are designated below the appropriate nucleotide triplet. Accordingly, M is methionine; K is lysine, P is proline; E is glutamate, L is leucine; T is threonine; A is alanine; S is serine; V is valine; F is phenylalanine; I is isoleucine; G is glycine; D is aspartic acid; Q is glutamine; R is arginine; C is cysteine; W is tryptophan; N is asparagine; H is histidine; and Y is tyrosine.

FIG. 4. Northern blot of total RNA isolated from infected larvae. Total RNA was isolated from *T. ni* larvae at 3 and 6 days post inoculation (PI) with TnGV. Ten micrograms of RNA were electrophoresed in a denaturing 1.5% agarose and northern blotted following the methods of Dwyer and Granados (17). Blots were probed with the internal KpnI fragment of TnGV-VEF gene under high stringency conditions. No hybridization was found to RNA isolated at 3 days PI. However, 2 RNA species of 2.7 and 3.3 Kbp hybridized at 6 days PI. This indicated that the VEF gene was probably a late gene.

FIG. 6. A comparison of the nucleotide sequence for the PuGV-H SF and TnGV VEF genes. Hyphens denote nucleotide identical to the PuGV-H sequence. The consensus baculovirus late promoters (30) have been underscored, the putative start codon has been bolded, and the stop codon overscored. Two frameshift mutations have occurred at +1962 and +1985. The homology between the two genes is 99.1%. The second open reading frame starts at +2755 nt. The stop codon for this gene has not been found.

FIG. 7. A comparison of the amino acid sequence for the PuGV-H SF and TnGV VEF proteins. Hyphens denote nucleotide identical to the PuGV-H sequence. The identity between the two proteins is 98.2%.

FIG. 8. SDS-PAGE analysis of purified SF and VEF. Three micrograms of VEF or SF was added to an equal volume of 2× SDS-PAGE loading buffer (0.125M Tris-HCl pH 6.8, 4% SDS, 20% glycerol, 10% 2-mercaptoethanol). The sample were electrophoresed for 4.5 hours at 30 mAmps through a 7% separating gel (10 cm×12 cm×1.5 mm), and stained with COOMASSIE blue R-250 following standard protocols. SF (lane 1) migrated at 106K while VEF (lane 2) migrated at 101K.

FIG. 9. SDS-PAGE analysis of in vitro digest of peritrophic membranes. Individual peritrophic membranes (PM) were dissected from the last instar (a) *Trichoplusia ni* and (b) *Pseudaletia unipuncta* larvae. Peritrophic membranes were resuspended in 50 μl of 0.1M $Na_2CO_3$ pH 10.5 containing (a) 5 μg or (b) 10 μg of VEF (lane 2) or SF (lane 3), and incubated at 28° C. for 60 min. The reactions were stopped by washing the PMs in deionized water and resuspending in SDS-PAGE loading buffer (0.062M Tris-HCl pH 6.8, 2% SDS, 5%—mercaptoethanol). Controls (ln 1) consisted of PMs treated in the same manner but without enhancing protein. Samples were electrophoresed through at 10% separating gel and silver stained. SF and VEF digested the same protein in both the *T. ni* and *P. unipuncta* PMs. Multiple degradation products are evident in both the SF (ln 3) and VEF (ln 2) lanes.

FIG. 10. SDS-PAGE and Western bolt analysis of nine baculoviruses. Viral occlusion bodies were dissolved in DAS (0.1M $Na_2CO_3$, 0.01M EDTA, 0.17M NaCl, pH 10.9) for 15 min at room temperature. An equal volume of 2× SDS-PAGE loading buffer (0.125M Tris-HCl pH 6.8, 4% SDS, 20% glycerol, 10% 2-mercaptoethanol was added and the samples electrophoresed through a 10% separating gel. The gels were either (a) stained with COOMASSIE blue (b) or used in Western blots. Proteins cross-reacting with an anti-VEF/TrpE (23) antiserum were found in CpGV (lane 1, 80 Kd), EaGV (Lane 2, 80 Kd), HaGV (lane 4, 110 Kd), PrGV (lane 7, 101 Kd) and PuGV-H (lane 8, 106 Kd). EeGV (lane 3), PbGV (lane 5), PiGV (lane 6), PuGV-O (lane 9) did not cross-react with the antiserum.

FIG. 11. SDS-PAGE and Western blot analysis of nine baculoviruses. Viral occlusion bodies were dissolved in DAS (0.1M $Na_2CO_3$, 0.01M EDTA, 0.17M NaCl, pH 10.9) for 15 min at room temperature. An equal volume of 2× SDS-PAGE loading buffer (0.125M Tris-HCl pH 6.8, 4% SDS, 20% glycerol, 10% 2-mercaptoethanol) was added and the samples electrophoresed through a 10% separating gel. The gels were either (a) stained with COOMASSIE blue (b) or used in Western blots. Proteins cross-reacting with an anti-VEF/TrpE (23) antiserum were found in StGV (lane 11, 106 Kd), and TnGV (lane 12, 104 Kd). SfGV (lane 10), AcMNPV (lane 13), AgMNPV (lane 14), CfNPV (lane 15), HzSNPV-ELCAR (lane 16), and TnSNPV (lane 17), did not cross-react with the antiserum.

DETAILED DESCRIPTION OF PREFERRED EMBODIMENTS

Enhancing Protein Purification

The TnGV VEF and PuGV-H SF were isolated according to the methods of Gallo et al. (21) with the following modifications. SEPHACRYL® and now replaced by SEPHARYL® S-300HR and the initial concentration of viral occlusion bodies was reduced from $1.7 \times 10^{12}$ to $1.0 \times 10^{12}$ per ml.

Purified enhancing factor containing approximately 3 mg of protein was added to an equal volume of 2× sample buffer (2×=0.125M TRIS HCl [Tris(hydroxymethyl) aminomethane]. pH 6.8, 4% SDS, 20% glycerol, 10% 2-mercaptoethanol), heated in a boiling water bath for 3 min., and separated by SDS polyacrylamide gel electrophoresis (PAGE) according to the methods of Laemmli (29). Electrophoresis was carried out at 30m Amps for 4.5 hr in a 7% separating gel (10 cm×12 cm×1.5 mm), and stained with COOMASSIE Blue R-250 following standard protocols.

Cloning and Sequencing of Enhancing Genes

The VEF present in granulin fraction of TnGV OBs was purified in the following manner:

$1.7 \times 10^{12}$ TnGV OBs were dissolved in 1 ml 0.05M $Na_2CO_3$ for 15 min. at room temperature, and layered on a 20% sucrose cushion in $H_2O$ and centrifuged for 45 min. at 126,000 g at 4° C. The granulin fraction remained on top of the sucrose cushion and was collected. After an incubation of 5 hrs at 28° C., the granulin fraction was applied onto a Sephacryl-S-200 column (2.6×34 cm) and eluted with 50 mM Tris-HCl pH 7.0, 0.1M NaCl at 1.5 ml/min, and the absorption of the eluate measured at 280 nm. The first peak containing VEF protein was poled and used for experiment.

Figure 1A:
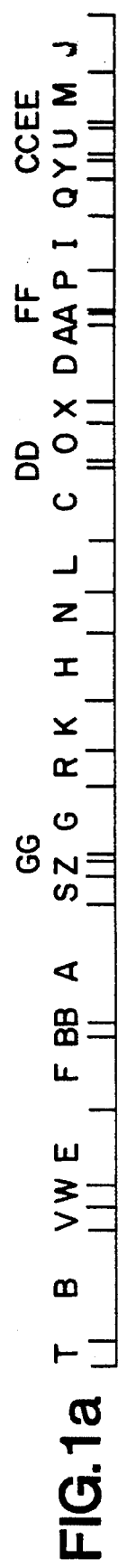
Figure 1B:
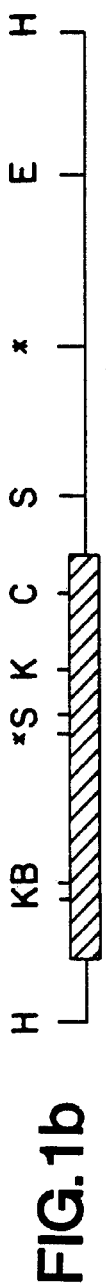
Figure 1C:
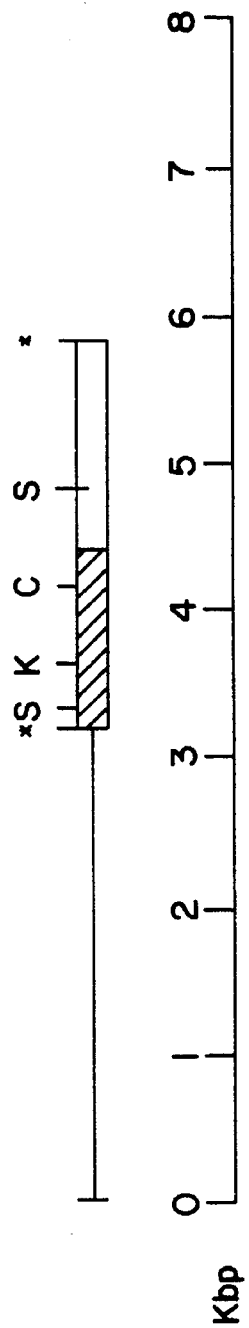
Figure 2:
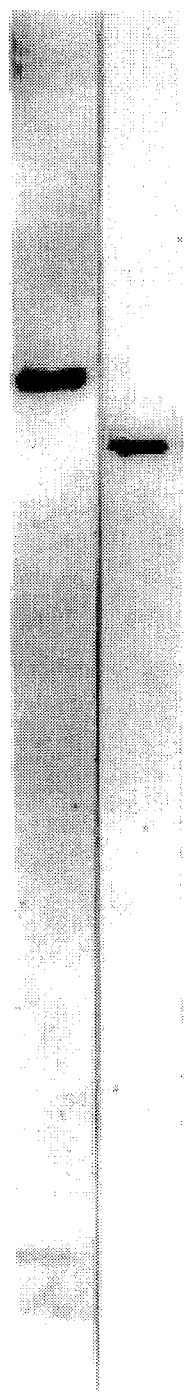

A cloning and expression vector, lambda gtll, was used for construction of genomic library of TnGV and for isolation of the VEF gene (3). Antibodies were raised against Sephacryl-column purified VEF from granulin fraction after alkali solubilization of OBs (1) and were used for immunoblotting to screen for positive clones. Through several steps of screening approximately 6000 plaques, a clone was selected containing the longest viral-VEF DNA insert. Southern blot hybridization analysis of TnGV DNA Hind III digests, probed with the VEF clone insert, revealed that the VEF gene existed on the Hind III-M fragment. Western blot analysis of the fusion protein expressed in lysogenic *E. coli* (Y1089 strain) transfected with VEF clone had a molecular weight of 153 kD (FIG. 2). This suggested a fusion protein gene consisting of 39 Kd of the VEF carboxy terminal end and the 114 Kd beta-gal gene (FIGS. 1c, 2). Since the VEF has a size of 104 Kd, the position of the VEF gene on a fine map of the Hind III-M fragment was predicted and a 3.5 kbp DNA portion was sequenced (Item b of FIG. 1).

Figure 4:
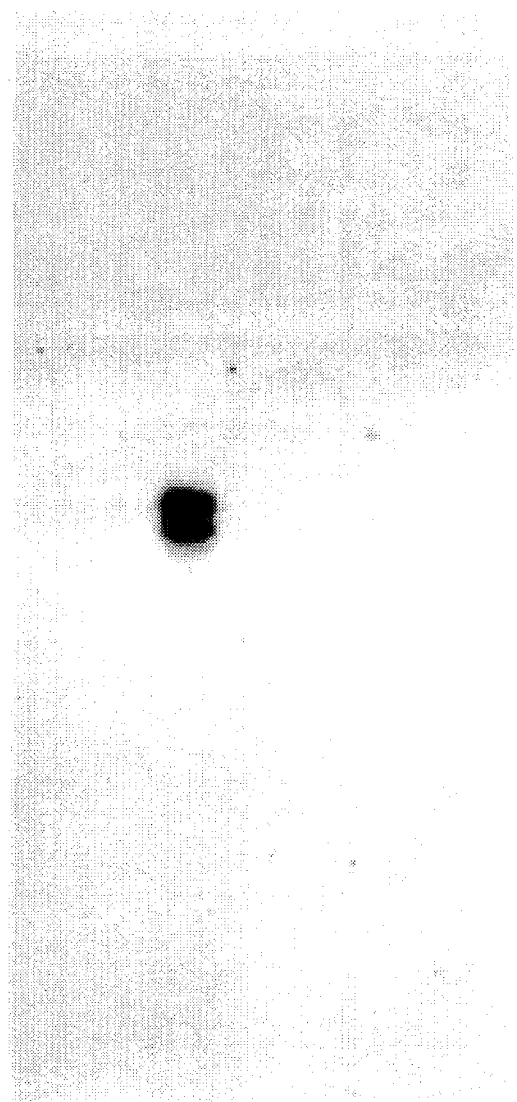
Figure 5A:
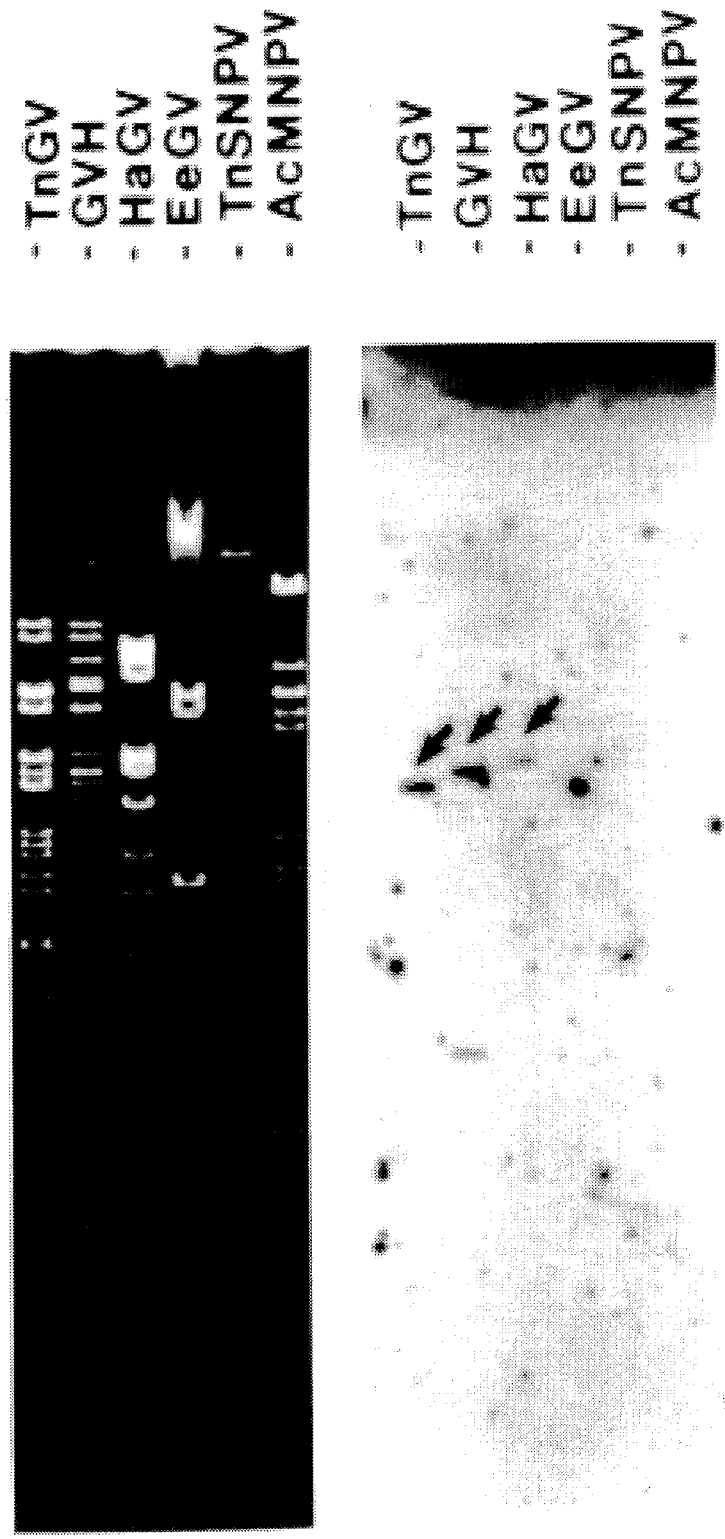
FIG. 5a and FIG. 5b. Southern hybridization and SDS-PAGE analysis of TnGV and 5 other baculoviruses. Item a of FIG. 5a) Genomic baculovirus was digested with Hind III and electrophoresed on a 0.75% agarose gel. The DNA was transferred to nitrocellulose and probed with the internal KpNI fragment of TnGV-VEF and washed under high stringency conditions. Homologous sequences were identified in PuGV-H, and HaGV. Item b of FIG. 5b) Occlusion bodies are dissolved in 0.05M NaCO pH 10.5 for 15 minutes at room temperature and the nucleocapsids pelleted by centrifugation at 14,000×g. The supernatants were removed and electrophoresed in a 10% SDS-PAGE gel and stained with COOMASSIE blue.
Figure 5B:
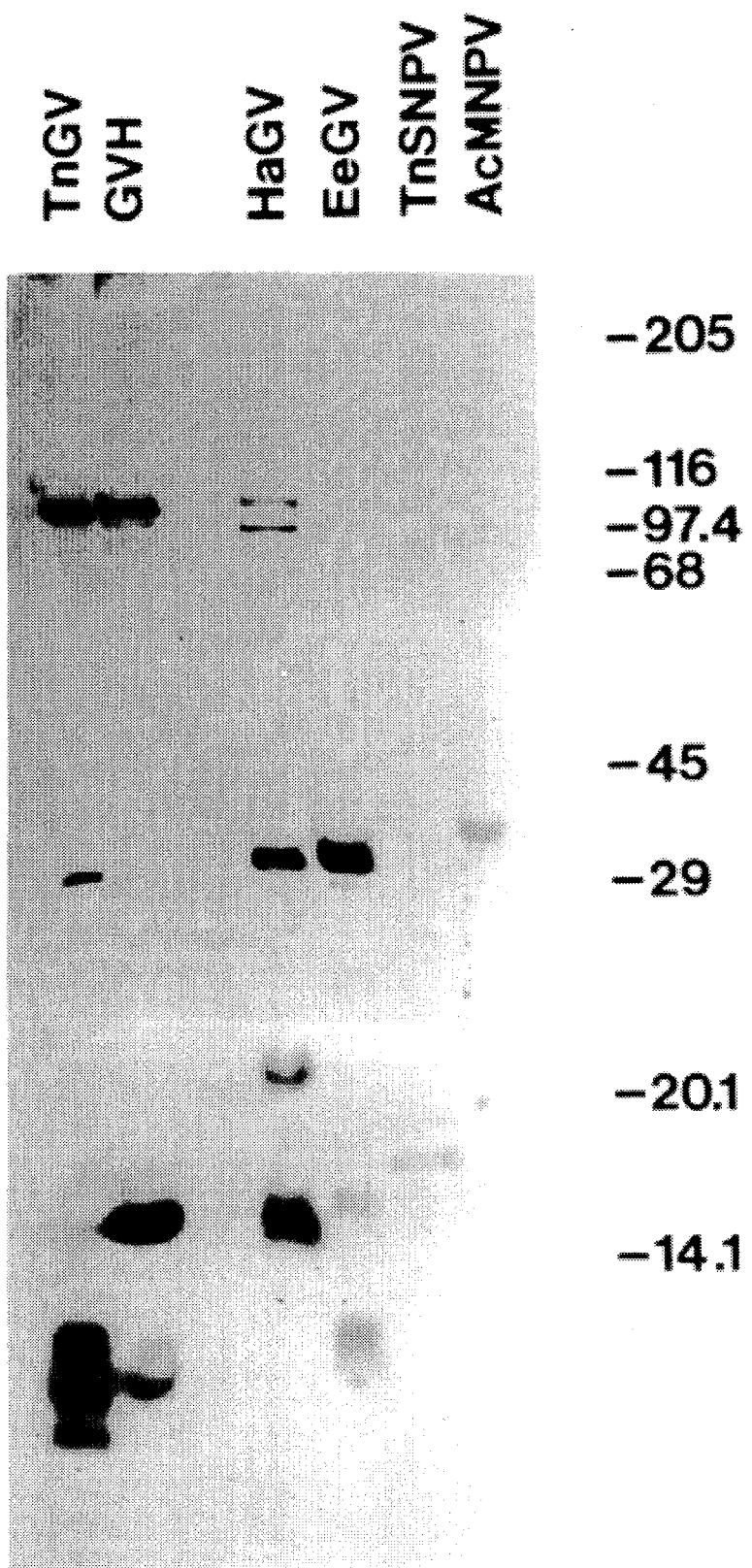

Sequence analysis showed an open reading frame of 2,703 bp DNA corresponding to the size of the VEF polypeptide at the predicted location of the VEF gene (FIG. 3). The deduced size of the polypeptide was 104,300 daltons and consisted of 901 amino acid residues. There are no sites for lipophilic modification. To determine the presence of the VEF gene among several isolates of baculovirus a 1.5 kbp portion of the VEF gene was probed onto a Southern blot of different virus DNA fragments digested with Hind III restriction enzyme under high stringency condition (12). The result showed that two granulosis virus DNAs, isolated from PuGV-H and HaGV, contained a sequence homologous to the TnGV VEF gene probe (FIG. 5a). DNA isolated from EeGV did not contain sequences homologous to the VEF gene probe. The restriction enzyme digestion pattern of DNA from TnGV, GVH, and HaGV were very similar, whereas EeGV exhibited a very distinct DNA profile. The probe did not hybridize with DNAs from two nuclear polyhedrosis viruses (FIG. 5a). Temporal gene expression of the VEF gene was examined by Northern blot analysis of total RNA from TnGV-infected *T. ni* larvae at 3 and 6 days p.i. A probe with a size of 1.5 Kb KpnI-V fragment, a part of the VEF gene, showed no hybridization with RNAs at 3 days p.i. but showed strong hybridization with two RNA species with sizes of 2.7 Kb and 3.3 Kb at 6 days p.i. (FIG. 4). The TnGV-VEF present in the granulin fraction of alkaline dissolved OBs was resolved as a 104 Kd protein on a SDS-polyacrylamide gel. To determine the presence of high molecular weight polypeptides in granulin or polyhedrin fractions from six baculoviruses, these virus samples were analyzed by SDS-PAGE (FIG. 5b). In the granulin fractions from TnGV, GVH and HaGV, polypeptides with a size of 104 Kd, 106 Kd, and a complex of 110 Kd and 94 Kd were detected, respectively. The single high molecular weight polypeptide (106 Kd) from GVH appears to migrate on SDS-PAGE similar to the 104 Kd protein from TnGV (FIG. 5b and Y. Tanada, personal communication). The assignment of a VEF function to either the 94 or 110 kDa polypeptides from HaGV is not clear at this time. No polypeptides with a size of approximately 100 kDa were present in EeGV, TnSNPV, and AcMNPV. Three of the GVs examined, TnGV, GVH, and HaGV all infect the noctuid species *T. ni*, whereas EeGV grows only in the sphyngid species, *E. ello*.

KpnI and SalI subclones of the EcoRI-I fragment of PuGV-H, which contains the entire SF gene, were cloned into the KpnI and SalI sites of pUC 19 (40). This was followed by nested deletions from both ends of the subcloned DNA using the Exo/mung deletion kit (Stratagene). The nucleotide sequence was determined using the dideoxy chain termination method of Sanger et al. (32) as modified for use with the Sequenase sequencing kit (U.S. Biochemicals). Sequencing data were compiled and analyzed using the PCGENE (Intelligenetics) software package.

Neonate bioassays employing 3–5 hr old larvae were conducted according to the methods of Hughes et al. (28) except that the neonates were not preselected for vigor and the droplets were applied by means of a syringe equipped with a blunt needle (26). The inoculum contained $1 \times 10^5$ OB/ml of AcMNPV with 1.0 or 0.5 mg/ml of either TnGV VEF or PuGV-H SF and all larvae were assumed to have imbibed 10 nl of inoculum (27). After ingestion of the inoculum, larvae were transferred with a fine paintbrush into individual 35 ml cups containing high wheat germ diet. Controls consisted of neonates that imbibed either virus without any enhancing factor or water with food coloring. The test was conducted 2 times with 30 larvae/treatment in each test group.

In Vitro Peritrophic Membrane Assay

PM were dissected from last instar *T. ni.* and *P. unipuncta* larvae, rinsed in deionized water to remove diet residue, and stored at −80° C. Thawed PMs were resuspended in 50 ml of digestion buffer (0.1M $Na_2CO_3$, pH 10.5) containing either 5 μg or 10 μg of SF or VEF. After incubation at 28° C. for 1 hr, the PMs were washed in water, placed in 1× SDS-PAGE sample buffer and boiled for 5 min. Controls consisted of PMs treated in the same manner but without any enhancing factor. The protein composition of the treated and control PMs were analyzed by discontinuous SDS-PAGE (79) on a Mini-PROTEAN II (BioRad) at 200 volts for 35 min with a 10% separating gel. Gels were stained using the BioRad Silver Staining Kit according to he manufacturer's instructions.

Western Blots

Viral occlusion bodies were first dissolved in dilute alkali solution (0.1M $Na_2CO_3$, 0.01M EDTA, 0.17M NaCl, pH 10.9) for 15 minutes at room temperature. An equal volume of 2× SDS-PAGE sample buffer was added and the mixture heated in a boiling water bath for 7 minutes. Samples were separated by SDS-PAGE as described above. The proteins were then electrophoretically transferred to nitrocellulose paper following the methods of Towbin et al (38). Western blots were analyzed using an anti-VEF/TrpE polyclonal antibody at a dilution of 1:5000 (23). Bands were visualized using an alkaline phosphatase conjugated secondary antibody (19).

SUMMARY OF RESULTS

For cloning and sequence analysis of VEF, two positive clones were identified from the approximately 6000 plaques screened with a α-VEF polyclonal antiserum. Both clones had identical inserts of 2.8 Kb mapped to the Hind III-M fragment of the TnGV genome (92.2 to 95.8 map units; FIG. 1a). Other TnGV fragments hybridizing to the clones included the 6.7 Kb EcoRI-K and the BamHI-FG doublet. Detailed maps of both TnGV Hind III-M and the insert DNA were generated using several restriction enzymes (FIGS. 1b,c).

Western blot analysis using both an anti-VEF polyclonal antisera and an anti-β-galactosidase monoclonal antibody (Promega, Madison, Wis.) demonstrated that the fusion protein generated by lambda-F had a molecular weight of 153 Kd which presumably consisted of 39 Kd of VEF carboxy-terminal and 114 Kd of β-galactosidase protein (FIG. 2). The VEF gene was tentatively positioned on the Hind III-M fragment using this information.

Sequence analysis of approximately 3.5 Kbp of Hind III-M DNA revealed an open reading frame of 2703 bp (901 amino acids) encoding a protein with a predicted molecular weight of 104.3 Kda (FIG. 3). The predicted protein contains 12 candidate sites for N-linked glycosylation (ASN/X/SER or Thr) and no sites predicted for lipophilic modification (LYS/X/X/CYS/X/X/ASN). A consensus baculovirus late promoter (ATAAG) occurred at −4 nt and a probable polyadenylation signal (AATAA) was found 2 nt downstream of the VEF ORF. The upstream region of the VEF gene contained three perfect repeats of the sequence TTACAAGA between −192 and −149 nt of the translation start site. Curiously, these repeats were similar to the baculovirus consensus sequence for hyperexpression described by Rohrman (5). However, in all three sequences, mismatches occurred at the invariable "T" of the "ATAAG" core late promoter motif. Changes at this position have been shown to eliminate transcriptional initiation (5). A comparison of the deduced amino acid sequence of the VEF with both the NBRF and Swiss-Prot protein data bases did not reveal any similarity to known proteins.

The occurrence of the late core promoter sequence at −4 bp indicated that VEF should be expressed late in infections. This was demonstrated by isolating RNA from infected larvae at several times (3 days and 6 days) PI. Using a restriction fragment from within the VEF open reading frame (ORF) as a probe, strong hybridization was shown to 2 RNA species (2.7 and 3.3 Kb) at 6 days PI but none at 3 days PI (FIG. 4). The transcript size of 2.7 Kb agreed with the predicted transcription start and stop signals adjacent to the open reading frame.

For SF sequence analysis, approximately 3300 bp within the EcoRI-I fragment of PuGV-H was sequenced, in both directions, revealing a 2703 bp open reading frame (ORF; FIG. 6) with a calculated molecular weight of the protein of 104 Kd. A consensus baculovirus late promoter motif (ATAAG; Ooi et al.) (30) was located at −8 to −4 nts relative to the ORF. A comparison of both the nucleotide and amino acid sequence with that of the VEF gene from TnGV revealed a 99.1% (FIG. 6) and 98.2% (FIG. 7) homology respectively. The only significant difference in homology between PuGV-H SF and TnGV VEF genes occurs between nucleotide +1962 and +1985. Two reciprocal frameshifts in the PuGV-H sequence have caused a 7 amino acid gap which shares no homology to the TnGV VEF protein sequence. Homology of the PuGV-H gene with the TnGV VEF gene was greater than 95% for 300 bp upstream of the gene. After this point, the homology decreases to 17.7%. From data analyzed thus far, the PuGV-H and TnGV sequence homology is greater than 99% for 155 nts downstream of the genes. A consensus baculovirus late promoter motif is located 35 nt upstream of the stop codon of the VEF and SF gene sequences, and 78 nt upstream of a potential ORF. This possible second ORF is located 43 nt downstream of the SF and VEF ORFs.

Figure 8:
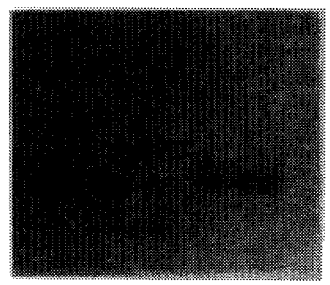

The enhancing protein from PuGV-H was purified from capsules in the same manner as the TnGV VEF. Approximately 330 mg of purified protein was isolated from $1.0 \times 10^{12}$ OBs. Based on SDS-PAGE analysis, purified SF had a calculated molecular weight of 106 Kd (FIG. 8). While this was in good agreement with the predicted molecular weight of 104 Kd from other protein sequence analysis there is a repeatable difference in the migration pattern when compared to the TnGV VEF protein (FIG. 8).

The homology between the VEF and SF proteins suggested that the ability to enhance baculovirus infections should also be similar. This was tested by a neonate larval bioassay (Table 1) and an in vitro PM assay (FIG. 9). Enhancement of AcMNPV infections of *T. ni* larvae occurred with the VEF and SF proteins. The 2.4 fold enhancement of

TABLE 1

Effect of PuGV-H and TnGV Enhancing Factors on AcMNPV Infections of *Tricloplusia ni* Neonate Larvae*

| Enhancing Factor | | Percent |
|---|---|---|
| Source | ng/larva | Mortality† |
| PuGV-H | 10 | 95 |
| PuGV-H | 5 | 95 |
| TnGV | 10 | 95 |
|  | 0 | 40 |

Figure 9A:
Figure 9B:
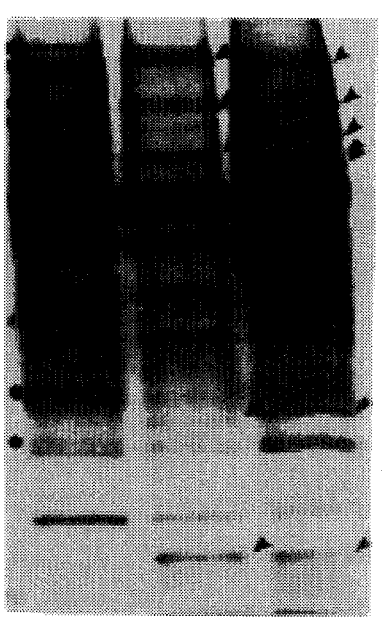

*All larvae were infected with 1 OB.
†This represents the average of two bioassays with 30 larvae per treatment. Non-virus control had no mortality.

infections by SF was identical to that seen in the VEF assays. In the in vitro PM assay, SF and VEF digested the same proteins in both the *T. ni* and *P. unipuncta* PMs. For the *T. ni* PM, 3 proteins of molecular weight 236.6 Kd, 111.5 Kd, and 98.2 Kd present in the control lanes are absent in the SF and VEF treatment lanes (FIG. 9a). Protein bands found only in the treatment lanes include a predominant group of bands occurring between 71.6K and 58.8K and 2 lower molecular weight proteins of 31.2K and 23.3K (FIG. 9a). In *P. unipuncta*, 7 proteins are absent in the treatment lanes as compared to the control (FIG. 9b, lane 1). The molecular weight of the digested bands are 210.5 Kd, 184.3 Kd, 171.1 Kd, 125.7 Kd, 111.5 Kd, 36.4 Kd, and 32.0 Kd. While there are 4 new protein bands of molecular weight 182.4 Kd, 121.3 Kd, 32.4 Kd, and 24.6 Kd common to both SF and VEF treatments, 4 unique proteins are also evident: 85.5K in VEF and 91.8K, 82.7K, and 80.0K in the SF treatment (FIG. 9b, lanes 2 and 3).

Figure 11B:
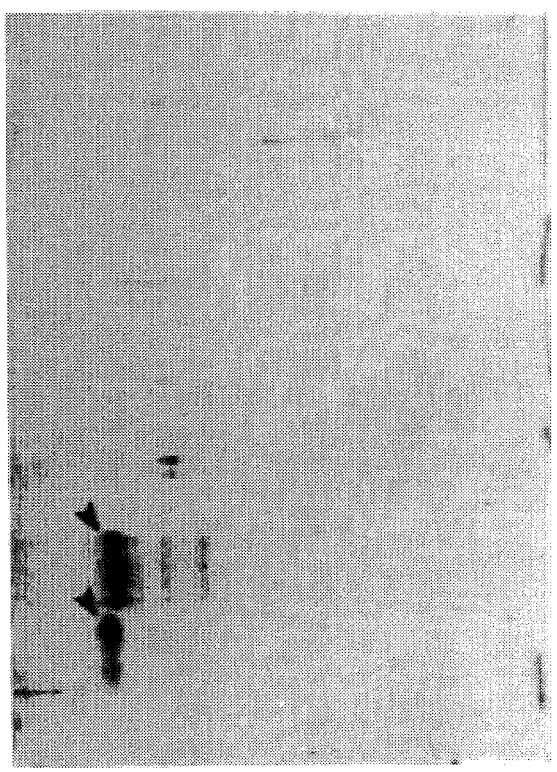
Figure 11A:
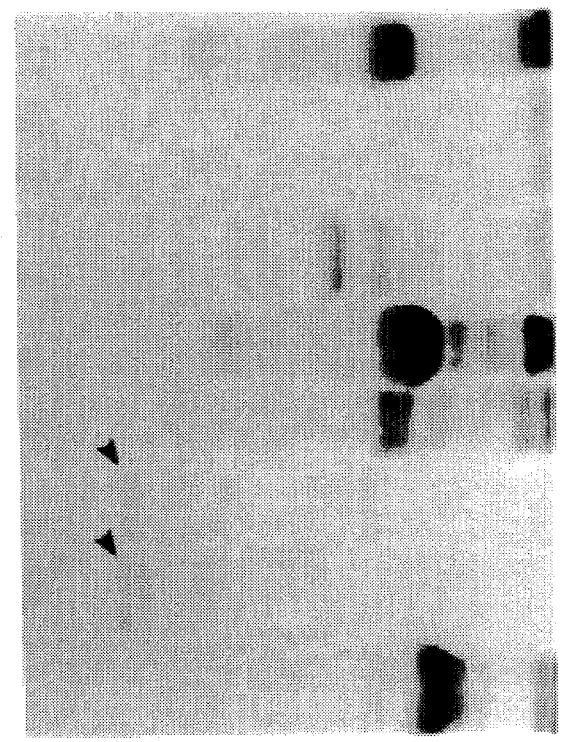

In order to ascertain the prevalence of the VEF gene within the Baculoviruses, 17 different baculoviruses (12 GVs and 5 NPVs) have been screened for VEF homologs using a polyclonal antisera specific for the TnGV VEF protein (FIGS. 10 and 11). Cross-reactive proteins were found in 7 GVs: *Cydia pomonella* GV (CgGV), *Estigmene acrea* GV (EaGV), HaGV, PrGV, PUGV, and StGV. This represents GVs which were isolated from 4 different families of Lepidoptera: Arctiidae, Noctuidae, Pieridae, and Tortricidae. EeGV, PuGV Oregon strain, *Plodia interpunctella* GV, *Pieris brassicae* GV, and *Spodoptera frugiperda* GV did not have any cross-reactive proteins. None of the NPVs (AcMNPV, *Anticarsia gemmatalis* MNPV, *Choristoneura fumiferana* NPV, *Helicoverpa zea* SNPV, and TnSNPV) reacted with the antisera.

The identified VEF cross-reactive proteins could be subdivided based on the molecular weight of the proteins. PrGV, PuGV-H, StGV, and TnGV had the most common protein size of approximately 104 Kd. HaGV had a slightly higher molecular weight (110 Kd) while CpGV and EaGV had a significantly lower molecular weight of approximately 80 Kd.

The cloning and sequencing of the SF gene from PuGV-H represents the second baculovirus enhancing factor to be sequenced to date. The high degree of homology between the PuGV-H and TnGV genes is unusual and indicates that there may be a strong selective pressure on the gene. Another possible explanation is that PuGV-H may be a variant of TnGV: however, this seems unlikely since the degree of homology decreases to 17.6% 300 bps upstream of the gene. In addition, there are significant differences in the restriction enzyme patterns of the two viral genomes (23). The identification of a second open reading frame may explain the high degree of homology (>99%) observed downstream of the two genes. The effect of this downstream gene on the expression of VEF or SF is unknown. On SDS-PAGE, the SF and VEF proteins show a consistent difference in mobility. Since these proteins have near identical molecular weights, it is possible that the two proteins may be processed or modified differently in the two hosts.

The results from both the neonate and in vitro PM assays demonstrate that the two proteins are very similar in activity. The observed differences in the digestion patterns of the PM proteins from both *T. ni* and *P. unipuncta* are probably due to quantitative differences in the amounts of the two enzymes. Evidence for this comes from the *T. ni* digests and the periodicity of the protein bands between 71.6 Kd and 58.8 Kd. The same bands are present in both the SF and VEF digests; however, the intensity of the bands differ. In the VEF digest (FIG. 9a, lane 2) the higher molecular weight bands predominate while in the SF digest (FIG. 9a), lane 3) the opposite is true. The data suggests a possible endoproteolytic type of cleavage in which the digestion in the SF reaction has proceeded further than in the VEF reaction.

Five baculoviruses were originally tested for the presence of VEF-homologous proteins by both DNA hybridization and SDS-PAGE analysis of dissolved occlusion bodies (FIGS. 4A and B). Hind III genomic digest of the 5 baculovirus DNAs under low stringency conditions, using a restriction fragment with the VEF ORF as a probe, showed homology between TnGV and 2 other granulosis viruses (PuGV-H and HaGV). No apparent homology was seen to either EeGV, TnSNPV, or AcMNPV (FIG. 5A).

To date, a total of 8 GVs have been reported to have enhancing proteins. Seven of the proteins cross-react with a polyclonal antiserum specific for the VEF from TnGV. The other enhancing factor, which is found in *Xestia c-nigrum* (23), has not been tested with the antiserum. Enhancing proteins have now been identified in baculoviruses isolated from four families of Lepidoptera: Arctiidae, Noctuidae, Pieridae, and Tortricidae. Previously, enhancing factors had only been identified in GVs infecting Noctuidae. This data lends credibility to the hypothesis that these enhancing proteins are common in GVs and are important baculovirus proteins which assist in the initial stages (PM penetration and virion adsorption) of larval infections. Applicants' inability to identify cross-reacting proteins in the NPVs suggests that while these viruses may have proteins which are functionally related to the GV enhancing factors (1), they are unrelated in primary amino acid sequence.

The identified baculovirus enhancing proteins can be tentatively separated into 3 distinct groups based on molecular weight: 104 Kd, 110 Kd, and 80 Kd. All of the research has concentrated on 2 enhancing factors from the same group, PuGV-H and TnGV (104 Kd).

The absence of a protein in PuGV-O which does not cross-react to the VEF antiserum, confirms earlier reports indicating that PuGV-O does not contain an enhancing factor (6) and that differences exist in the capsular components of PuGV-H and PuGV-O (34,41).

It is important to note that the baculoviruses are just one of many insect pathogenic organisms that have evolved mechanisms, both behavioral and structural, to circumvent the PM (25) and *Babesia microti*, an intraerythrocytic piroplasm of the tick *Ixodes dammini*, has developed a complex "arrowhead" structure which secretes a series of digestive enzymes to enable passage through the PM (31).

The VEF and SF genes of the present invention can be used in engineering new viral pesticides with enhanced efficacy. For example, it can be used alone as biopesticide or in combination with known biological insecticides such as BT or with synthetic chemical insecticides. The gene product of this invention can also be used to produce VEF or SF in any microbial production system, e.g. *E. coli,* Bacillus or Streptococcus. It can be introduced into a variety of hosts such as plants for protection against insects or microbes as biologically active agents.

The genes of this invention can be engineered to be expressed in transgenic plants and as insects feed on these plants, they would ingest a constant dose of the factor. While the exact effect of this on the insect is undetermined, it can be hypothesized that prolonged disruption of the peritrophic membrane (PM) may allow opportunistic microbes to infect and kill the insects. It was recently found that the viral factor increases the efficiency of Bt delta endotoxin by removing a major mechanical barrier—the PM.

The genes of the present invention have been found to play a significant role as a determinant of virulence at the initial stage of infection in insect hosts. Knowledge gained in cloning and sequencing the viral gene should prove useful in helping to unravel the mechanism(s) of enhanced virus infection by enhancement factors present within the occlusion body matrix.

Notwithstanding that reference has been made to particular preferred embodiments, it will be understood that the present invention is not to be construed as limited as such, but rather to the lawful scope of the appended claims. In other words, the subject invention includes not only the specific nucleotide sequences depicted herein, but also all equivalent nucleotide sequences coding for molecules with substantially the same biological activity of enhancing the infectivity of baculoviruses. The term "equivalent" is being used in ordinary patent usage here as denoting a nucleotide sequence which performs substantially as the nucleotide sequence identified herein to produce molecules with substantially the same biological activity in essentially the same kind of hosts. Within this definition are subfragments which have biological activity of enhancing the infectivity of baculoviruses.

Inasmuch as the protein, i.e., the gene product, of the present invention has been defined by means of deductive amino acid sequencing, c.f. FIG. 3, it is to be understood that for this particular protein, embraced herein, natural allelic variations exist and occur from individual to individual. These variations may be demonstrated by (an) amino acid difference(s) in the overall sequence or by deletions, substitutions, insertions, inversions or additions of (an) amino acid(s) in said sequence. All such allelic variations are included within the scope of the present invention.

BIBLIOGRAPHY

1. Derksen, A. G. S. and Granados, R. R. *Virology* 167: 242–250 (1988).
2. Peters, W. and Wiese, B. *J. Insect Physio.* 32:43–49 (1986).
3. Snyder, M., Sweatser, D., Young, R. A. and Davis, R. W. *Meth. Enzym.* 154:107–128 (1985).
4. Vlak, J. M. and Smith, G. E. *J. Virol.* 41:1118–1121 (1982).
5. Rohrmann, G. F. *J. Gen. Virol.* 67:1499–1513 (1986).
6. Tanada, Y. and Hukuhara, T. *J. Invertebr. Pathol.* 17:116–126 (1971).
7. Tanada, Y. and Hara, S. *Nature* 254: 328–329 (1975).
8. Tanada, Y. *J. Insect Pathol.* 1:215–231 (1959).
9. Tanada, Y. Inoue, H., Hess, R. T. , and Omi, E. M. *J. Inverebr. Pathol.* 35:249–255 (1980).
10. Tanada, Y. *J. Invertebr. Pathol.* 45:125–138 (1985).
11. Yamamoto, T., Kita, H. and Tanada, Y. *J. Gen. Virol.* 45:371–381 (1979).
12. Maniatis, T., Fritsch, E. F. and Sambrook, J. *Molecular Cloning: A Laboratory Manual.* Cold Spring Harbor Laboratory, Cold Spring Harbor, N.Y. (1982).
13. Hamm, J. J. and Paschke, J. D. *J. Insect Pathol.* 5:187– 197 (1963).
14. Whitlock, V. H. *J. Invertebr. Pathol.* 23: 70–75 (1974).
15. Granados, R. R. and Williams, K. A. *The Biology of Baculoviruses,* CRC Press, Fl. Vol I:89–108 (1986).
16. Miller, L. K. *The Biology of Baculoviruses,* CRC Press, Fl. Vol I:217–238 (1986).
17. Dwyer, K. G. & Granados, R. R. *J. Virol.* 62: 1535–1542 (1988).
18. Jacques R. P. *Can. Entomol.* 120:575–580 (1988).
19. Sears, M. K. et al. *J. Econ. Entomology* 76:368–374 (April 1983).
20. Blake, M. S., Johnston, K. H., Russel-Jones, G. J. & Gotschlich, E. C. *Analyical Biochemistry* 136, 175–179 (1984).
21. Gallo, L. G., Corsaro, B. G., Hughes, P. R. & Granados, R. R. *Journal of Invertebrate Pathology* 58:203–210 (1991).
22. Goto, C. *Applied Entomology and Zoology* 25, 135–137 (1990).
23. Hashimoto, Y., Corsaro, B. G. & Granados, R. R. *Journal of General Virology* 72, 2645–2651 (1991).
24. Hara, S., Tanada, Y. & Omi, E. M. *Journal of Invertebrate Pathology* 27, 115–124 (1976).
25. Huber, M., Cabib, E. & Miller, L. H. *Proceedings of the National Academy of Sciences, U.S.A.* 88,2807–2810 (1991).
26. Hughes, P. R. & Wood, H. A. *Journal of Invertebrate Pathology* 37, 154–159 (1981).
27. Hughes, P. R., Wood, H. A., Burand, J. P. & Granados, R. R. *Journal of Invertebrate Pathology* 43, 343–350 (1984).
28. Hughes, P. R., van Beek, N. A. M. & Wood, H. A. *Journal of Invertebrate Pathology* 48, 187–192 (1986).
29. Laemmli, U. K. *Nature London* 227,680–685 (1970).
30. Ooi, B. G., Rankin, C., & Miller, L. K. *Journal of Molecular Biology* 210,721–736 (1989).
31. Rudzinska, M. A., Spielman, A., Lewngrub, S., Piesman, J. & Karakshian, S. *Cell and Tissue Research* 221, 471–481 (1982).
32. Sanger, F., Nicklen, S. & Coalson, A. R. *Proceedings of the National Academy of Sciences, U.S.A.* 74, 5463–5467 (1977).
33. Tanada, Y. & Hukuhara, T. *Journal of Invertebrate Pathology* 12, 262–268 (1968).
34. Tanada, Y. & Watanabe, H. *Journal of Invertebrate Pathology* 18, 307–312 (1971).

35. Tanada, Y., Himeno, M. & Omi, E. M. *Journal of Invertebrate Pathology* 21, 31–40 (1973).
36. Tanada, Y., Hess, R. T. & Omi, E. M. *Journal of Invertebrate Pathology* 26, 99–104 (1975).
37. Tanada, Y., Hess, R. T., Omi, E. M. & Yamamoto, T. *Microbios* 37, 87–93 (1983).
38. Towbin, H., Staehelin, R. & Gordon, J. *Proceedings of the National Academy of Sciences, U.S.A.* 76, 4350–4354 (1979).
39. Uchima, K., Harvey, J. P., Omi, E. M. & Tanada, Y. A. *Insect Biochemistry* 18, 645–650 (1988).
40. Vieira, J. & J. Messing. *Gene* 19, 259–286 (1982).
41. Yamamoto, T. & Tanada, Y. *Journal of Invertebrate Pathology* 32, 158–170 (1978).
42. Yamamoto, T. & Tanada. Y. *Virology* 107, 434–440 (1980).
43. Zhu, Y., Hukuhara, T. & Tamura, K. *Journal of Invertebrate Pathology* 54, 49–56 (1989).

What is claimed is:

1. An isolated and purified enhancin found in granulosis viruses obtained from within the vital occlusion body, said enhancin retaining the physical, chemical and biological properties of the enhancin of FIG. 3 or the PuGV DNA of FIG. 6, said enhancin purified by centrifugation and chromatography on a Sephacryl column and displays on a SDS-PAGE analysis no multiple bands and has a disruptive effect on the insect peritrophic membrane proteins and/or interacts with the midgut epithelium in such a manner as to effect the increased absorption, penetration, and uptake of virus by midgut cells with a concomitant increase in host mortality, the percent increase in mortality exceeding 50% when 10 ng of said enhancin per larvae is mixed with *Autographa california* nuclear polyhedrosis (AcMNPV) inoculum for infection of *Trichoplusia ni* larvae.

2. The enhancin of claim 1 encoded by a viral DNA having the PuGV-H or the TnGV nucleotide sequence shown in FIG. 6 and purified by centrifugation and chromatography on a Sephacryl column to the degree it displays no multiple bands on a SDS-PAGE analysis.

3. An isolated enhancin purified by passage through a Sephacryl column to give a viral enhancing factor having a molecular weight between 80 Kd and 110 Kd based on SDS-PAGE analysis, said enhancin being found in granulosis viruses obtained from within the viral occlusion body, and retains the physical, chemical and biological properties of the enhancin of FIG. 3 or the PuGV-H DNA of FIG. 6, which enhancin has a disruptive effect on the insect peritrophic membrane proteins and/or interacts with the midgut epithelium in such a manner as to effect the increased adsorption, penetration, and uptake of virus by midgut cells with a concomitant increase in host mortality, the percentage increase in mortality exceeding 50% when 10 ng of said enhancin per larvae is mixed with *Autographa california* nuclear polyhedrosis virus (AcMNPV) inoculum for infection of *Trichoplusia ni* larvae.

4. An isolated and purified enhancin of claim 1 obtained from viruses selected from one of the following families of lepidoptera consisting of: Arctidae, Noctuidae, Pieridae and Tortricidae.

5. The enhancin of claim 1 having molecular weight of 104 Kd.

6. A biopesticide comprising an enhancin of claim 1.

7. A composition comprising an enhancin of claim 1 and a pesticide.

8. A toxicant composition to insects comprising an enhancin of claim 1 and synthetic chemical insecticide.

* * * * *

UNITED STATES PATENT AND TRADEMARK OFFICE
CERTIFICATE OF CORRECTION

PATENT NO. : 5,475,090
DATED : December 12, 1995
INVENTOR(S) : Granados et al

It is certified that error appears in the above-indentified patent and that said Letters Patent is hereby corrected as shown below:

IN THE DRAWINGS:

Sheet 9, Fig. 6A, line 1, please correct the 9th-11th nucleotides "ATG" to read --ATG--.

Sheet 10, Fig. 6B, line 22, please correct the 11th-16th nucleotides "TCTAAT" to read --$\overline{\text{TCTAAT}}$--.

Signed and Sealed this

Twenty-ninth Day of October 1996

Attest:

BRUCE LEHMAN

Attesting Officer     Commissioner of Patents and Trademarks

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 3556 basepairs
        ( B ) TYPE: Nucleic acid
        ( C ) STRANDEDNESS: Doublestranded
        ( D ) TOPOLOGY: Circular ( i i ) MOLECULE TYPE: Genomic DNA ( i i i ) HYPOTHETICAL: No ( i v ) ANTI-SENSE: No ( v ) FRAGMENT TYPE: N/A ( v i ) ORIGINAL SOURCE:
        ( A ) ORGANISM: Trichoplusia ni granulosis virus ( v i i ) IMMEDIATE SOURCE:
        ( A ) LIBRARY: Lambda GT11
        ( B ) CLONE: HindIII-M ( v i i i ) POSITION IN GENOME:
        ( A ) CHROMOSOME/SEGMENT: N/A
        ( B ) MAP POSITION: 92.2 - 94.2
        ( C ) UNITS: genome percent ( i x ) FEATURE:
        ( A ) NAME/KEY: Mature protein
        ( B ) LOCATION: 435 bp to 3140 bp
        ( C ) IDENTIFICATION METHOD: Experimentally
        ( D ) OTHER INFORMATION: Degrades special Peritrophic
            Membrane proteins. Binds to midgut brush border ( i x ) FEATURE:
        ( A ) NAME/KEY: Baculovirus very late promoter
        ( B ) LOCATION: 427 to 432 bp
        ( C ) IDENTIFICATION METHOD: Experimentally
        ( D ) OTHER INFORMATION: N/A ( i x ) FEATURE:
        ( A ) NAME/KEY: Possible glycosylation sites
        ( B ) LOCATION: Site 1 65 to 67 amino acids
            Site 2 265 to 267 amino acids
            Site 3 306 to 308 amino acids
            Site 4 339 to 341 amino acids
            Site 5 349 to 351 amino acids
            Site 6 540 to 542 amino acids
            Site 7 594 to 596 amino acids
            Site 8 595 to 597 amino acids
            Site 9 621 to 623 amino acids
            Site 10 642 to 644 amino acids
            Site 11 683 to 685 amino acids
            Site 12 698 to 700 amino acids
        ( C ) IDENTIFICATION METHOD: Experimentally
        ( D ) OTHER INFORMATION: Not known ( x i ) SEQUENCE DESCRIPTION: SEQUENCE ID NO: 1:

```
CAGCGCGAAA ACGGTTGGTG CCAATTACTG GTATATTGCT ATGATCGAGT CACGTCATAA      60

GGGTCGATTC GCGACGGTCT CCCACGTGGC CTTCCATTGA GGTTTACGTG TTTGTGTATG     120

CGTGCGAGTG TTTTTATAAC CCAAAAACTC AGCCACACCG TGTCCACCGT ACATATACTT     180

GTCCTTTTCC AATTCCACAA TCCAAATTTC CGCAGAAACT CCTCCAATGT TGCACGATTT     240

TTTTACAAGA GTCATTTTGC ACGTTTACAA GAAATTTATT ACAAGATTAG CTGCTTGTGA     300

TAAAGGTCTG CACGAGATGA GATTCAAATA CGTAATGAGA ATTGCGTGAT TTGCACGAGT     360

TTATATAGCA TAATTTGCTA GGAATGTCTG TTGGTTTGTG ATGTTTAGGT GTTCGCTGCA     420

TTAATTATAA GACT ATG TCG TAC AAA GTG ATT GTA CCC GCT ACC GTG CTA      470
             Met Ser Tyr Lys Val Ile Val Pro Ala Thr Val Leu
              1           5                       10
```

| | | | | | | | | | | | | |
|---|---|---|---|---|---|---|---|---|---|---|---|---|
| CCG | CCG | TGG | CTC | AGA | GTC | GGT | GAG | AAT | TGG | ATA | TTC GCA AGA CAC AGA | 518 |
| Pro | Pro | Trp | Leu | Arg | Val | Gly | Glu | Asn | Trp | Ile | Phe Ala Arg His Arg | |
|  |  | 15 |  |  |  | 20 |  |  |  |  | 25 | |

```
CGC ACC GAG GTG GGA GTC GTT CTA CCG GCG AAC ACG AAA TTT CGT GTA      566
Arg Thr Glu Val Gly Val Val Leu Pro Ala Asn Thr Lys Phe Arg Val
     30              35                  40

CGA GCA GAT TTC TCT AGG GCC GGC TTC ACC CGA CCC GTA ATA GTG CGC      614
Arg Ala Asp Phe Ser Arg Ala Gly Phe Thr Arg Pro Val Ile Val Arg
45              50                  55                      60

CTC TTG AAC AAC AAC CGT AGC ACT GAA CGA GAA ATC AAC TTG AAC AAC      662
Leu Leu Asn Asn Asn Arg Ser Thr Glu Arg Glu Ile Asn Leu Asn Asn
                65              70                  75

GAC CAA TGG ATG GAG GTG GAG CAT GCG CAC GAG AGT GTG CCT TTC GTA      710
Asp Gln Trp Met Glu Val Glu His Ala His Glu Ser Val Pro Phe Val
            80                  85                  90

GAT TGG CTG GTG GGC GAA AAG AAC ACT ATG GCC GAA GTG TAT TTT GAA      758
Asp Trp Leu Val Gly Glu Lys Asn Thr Met Ala Glu Val Tyr Phe Glu
        95                  100                 105

ATC GAC GGA CCA CAC ATA CCG CTA CCC GTG TAC GTG TTC AAC ACG AGA      806
Ile Asp Gly Pro His Ile Pro Leu Pro Val Tyr Val Phe Asn Thr Arg
    110                 115                 120

CCC GTC GAA CAC TTT AAG AGC GAG TAT CGC CAA AGT TCG TCT GGC TAC      854
Pro Val Glu His Phe Lys Ser Glu Tyr Arg Gln Ser Ser Ser Gly Tyr
125                 130                 135                 140

TGC TTT CTA TAT TTG GAC CTG GTC TGT ATG TTG GTA CCG CCC GCT AGC      902
Cys Phe Leu Tyr Leu Asp Leu Val Cys Met Leu Val Pro Pro Ala Ser
                145                 150                 155

AAA AAC GCT TTA TTG GAC GTG AAC ATT TTC GAG CTT CAT CAA TTT TAT      950
Lys Asn Ala Leu Leu Asp Val Asn Ile Phe Glu Leu His Gln Phe Tyr
            160                 165                 170

AAC GAA ATC ATT AAT TAC TAT GAT GAC CTG TGC GGC TTG GTC GAG GAT      998
Asn Glu Ile Ile Asn Tyr Tyr Asp Asp Leu Cys Gly Leu Val Glu Asp
        175                 180                 185

CCA TAC GCA GAC ACT GTC GAT TCG AAT TTA CCC AAC AAG GCT GCT TTC     1046
Pro Tyr Ala Asp Thr Val Asp Ser Asn Leu Pro Asn Lys Ala Ala Phe
    190                 195                 200

GTG AAA GCT GAT GCT GGC GGT CCG GGT GGT GCG TAT TAT GGA CCA TTT     1094
Val Lys Ala Asp Ala Gly Gly Pro Gly Gly Ala Tyr Tyr Gly Pro Phe
205                 210                 215                 220

TGG ACG GCA CCG GCG AGC TCA AAC CTT GGT GAT TAC CTC AGA ATA TCG     1142
Trp Thr Ala Pro Ala Ser Ser Asn Leu Gly Asp Tyr Leu Arg Ile Ser
                225                 230                 235

CCG ACC AAC TGG ATG GTA ATT CAC GAG CTG GGT CAT GCA TAC GAT TTT     1190
Pro Thr Asn Trp Met Val Ile His Glu Leu Gly His Ala Tyr Asp Phe
```

-continued

```
                      240                              245                              250
GTG   TTT   ACC   GTC   AAC   ACT   ATA   CTC   ATT   GAA   ATT   TGG   AAC   AAC   TCT   TTA         1238
Val   Phe   Thr   Val   Asn   Thr   Ile   Leu   Ile   Glu   Ile   Trp   Asn   Asn   Ser   Leu
            255                           260                          265

TGC   GAT   CGC   ATC   CAA   TAC   AAG   TGG   ATG   AAC   AAA   ATT   AAA   AGA   CAA   CAA         1286
Cys   Asp   Arg   Ile   Gln   Tyr   Lys   Trp   Met   Asn   Lys   Ile   Lys   Arg   Gln   Gln
270                           275                           280

CTG   GCT   CGC   GTC   TAT   GAA   AAT   AGA   CGA   CCG   CAG   AAA   GAG   GCG   ACC   ATT         1334
Leu   Ala   Arg   Val   Tyr   Glu   Asn   Arg   Arg   Pro   Gln   Lys   Glu   Ala   Thr   Ile
285                           290                           295                           300

CAG   GCG   CTG   ATC   GAC   AAT   AAC   AGC   CCG   TTC   GAT   AAT   TGG   GGC   TTT   TTT         1382
Gln   Ala   Leu   Ile   Asp   Asn   Asn   Ser   Pro   Phe   Asp   Asn   Trp   Gly   Phe   Phe
                        305                           310                           315

GAG   AGG   CTG   ATA   ATA   TTC   ACG   TGG   CTG   TAC   AAC   CCG   CAA   AGA   GGA   CTA         1430
Glu   Arg   Leu   Ile   Ile   Phe   Thr   Trp   Leu   Tyr   Asn   Pro   Gln   Arg   Gly   Leu
                  320                           325                           330

GAC   ACA   TTG   CGT   AAC   ATC   AAC   CAT   TCG   TAC   AGG   GTG   CAC   GCC   ACC   CGC         1478
Asp   Thr   Leu   Arg   Asn   Ile   Asn   His   Ser   Tyr   Arg   Val   His   Ala   Thr   Arg
            335                           340                           345

AAC   TCT   TCT   ATA   CCG   TAC   CCG   CAA   ATA   TGG   TCA   TGG   CTA   ACG   ACT   TCT         1526
Asn   Ser   Ser   Ile   Pro   Tyr   Pro   Gln   Ile   Trp   Ser   Trp   Leu   Thr   Thr   Ser
350                           355                           360

GCT   TAC   GAC   AAC   TTT   TGG   TTA   TAT   TTT   AAT   TTG   GTA   GGC   GTG   TAC   CCG         1574
Ala   Tyr   Asp   Asn   Phe   Trp   Leu   Tyr   Phe   Asn   Leu   Val   Gly   Val   Tyr   Pro
365                           370                           375                           380

GCA   GAC   TTT   TAC   GTA   AAC   GAA   CAC   AAC   AAA   GTT   GTT   CAT   TTC   AAT   CTA         1622
Ala   Asp   Phe   Tyr   Val   Asn   Glu   His   Asn   Lys   Val   Val   His   Phe   Asn   Leu
                        385                           390                           395

CAC   TTG   AGA   GCT   TTG   GCG   TTG   GGG   CAG   AGT   GTG   CGT   TAT   CCC   ATT   AAA         1670
His   Leu   Arg   Ala   Leu   Ala   Leu   Gly   Gln   Ser   Val   Arg   Tyr   Pro   Ile   Lys
                  400                           405                           410

TAT   ATA   ATT   ACA   GAC   TTT   GAT   CTG   GTG   AGC   AAA   AAC   TAC   GAC   ATT   AAA         1718
Tyr   Ile   Ile   Thr   Asp   Phe   Asp   Leu   Val   Ser   Lys   Asn   Tyr   Asp   Ile   Lys
            415                           420                           425

CAG   TAT   TTA   GAG   AGT   AAT   TTC   GAT   CTG   GTT   ATA   CCA   GAA   GAA   TTG   CGG         1766
Gln   Tyr   Leu   Glu   Ser   Asn   Phe   Asp   Leu   Val   Ile   Pro   Glu   Glu   Leu   Arg
430                           435                           440

CAG   ACC   GAT   TTG   TTG   GCG   GAC   GTG   AGG   GTG   GTT   TGT   GTG   ATT   GAC   GAT         1814
Gln   Thr   Asp   Leu   Leu   Ala   Asp   Val   Arg   Val   Val   Cys   Val   Ile   Asp   Asp
445                           450                           455                           460

CCG   TCG   CAG   ATT   GTG   GGC   GAA   CCG   TTT   AGC   GTG   TAC   GAC   GGG   AAC   GAG         1862
Pro   Ser   Gln   Ile   Val   Gly   Glu   Pro   Phe   Ser   Val   Tyr   Asp   Gly   Asn   Glu
                        465                           470                           475

CGA   GTG   TTC   GAG   AGT   ACG   GTG   GCC   ACG   GAC   GGA   AAC   ATG   TAT   CTG   GTG         1910
Arg   Val   Phe   Glu   Ser   Thr   Val   Ala   Thr   Asp   Gly   Asn   Met   Tyr   Leu   Val
                  480                           485                           490

GGC   GTG   GGT   CCG   GGA   GTG   TAC   ACG   TTG   CGT   GCG   CCA   CGC   GGC   AAA   AAC         1958
Gly   Val   Gly   Pro   Gly   Val   Tyr   Thr   Leu   Arg   Ala   Pro   Arg   Gly   Lys   Asn
            495                           500                           505

AAA   CGC   TAC   AAA   CTC   CAT   TTG   GCA   CAT   TCG   CCC   AGA   GAG   CCC   GTT   CAT         2006
Lys   Arg   Tyr   Lys   Leu   His   Leu   Ala   His   Ser   Pro   Arg   Glu   Pro   Val   His
510                           515                           520

CCG   GCC   AAC   GAC   CAC   ATG   TAT   CTG   CTC   GTG   ACG   TAT   CCC   TAC   TAC   AAT         2054
Pro   Ala   Asn   Asp   His   Met   Tyr   Leu   Leu   Val   Thr   Tyr   Pro   Tyr   Tyr   Asn
525                           530                           535                           540

CAA   ACG   TTG   ACA   TAC   ACA   CCG   TAC   GTA   AAT   TCT   GAC   CTA   GCC   GTC   GAC         2102
Gln   Thr   Leu   Thr   Tyr   Thr   Pro   Tyr   Val   Asn   Ser   Asp   Leu   Ala   Val   Asp
                        545                           550                           555

ATG   GCT   CAT   TTG   TTC   GGC   AGC   AAC   GAT   CGT   AGG   TAT   GTA   GCC   ACG   ATA         2150
```

```
Met Ala His Leu Phe Gly Ser Asn Asp Arg Arg Tyr Val Ala Thr Ile
        560                 565                 570

TAT TTC AAT CCA TTC GAA CAA ACA GTC ACC GTA CAT CTA AAC AAT ATT         2198
Tyr Phe Asn Pro Phe Glu Gln Thr Val Thr Val His Leu Asn Asn Ile
        575                 580                 585

CGT GCC GGT CGT GAA AAC AAC ACT ACC CTG TAC TTT GAA ATG GTA ATT         2246
Arg Ala Gly Arg Glu Asn Asn Thr Thr Leu Tyr Phe Glu Met Val Ile
        590                 595                 600

AGC AAC CCG TTC AAC GGG CAG AGC CAA ACT TTC ACT ATA CTC GAA GAC         2294
Ser Asn Pro Phe Asn Gly Gln Ser Gln Thr Phe Thr Ile Leu Glu Asp
605                 610                 615                 620

AAT CCC ACT TTA CGA CAA GGC TAC TAC AAA TTT GAC GTG GTC ACG TAC         2342
Asn Pro Thr Leu Arg Gln Gly Tyr Tyr Lys Phe Asp Val Val Thr Tyr
                625                 630                 635

AGC TCC ATA AGG CTG AAT ATG AGC GTC GCG GGT CGG CTA TTA TTT CGG         2390
Ser Ser Ile Arg Leu Asn Met Ser Val Ala Gly Arg Leu Leu Phe Arg
                640                 645                 650

CGA TAC ATT TTT GCC GGA GGT ACC ACC ACG CTG ACC ATG TTC CCA AAT         2438
Arg Tyr Ile Phe Ala Gly Gly Thr Thr Thr Leu Thr Met Phe Pro Asn
        655                 660                 665

CAA GTA CTT GAG CCC AAT TTG TTT CCA GAC GGT TCC GCC TTG AAT AGG         2486
Gln Val Leu Glu Pro Asn Leu Phe Pro Asp Gly Ser Ala Leu Asn Arg
670                 675                 680

ACA TTG GCA CGA CTA AGA GAA CAG GCC GCC TTC CTA GAT AAT TAT TCA         2534
Thr Leu Ala Arg Leu Arg Glu Gln Ala Ala Phe Leu Asp Asn Tyr Ser
685                 690                 695                 700

CAA CTT ATG TAT ATT GAA AAC GAG TTG CGC GAC ACG ATT TAT TTG GCC         2582
Gln Leu Met Tyr Ile Glu Asn Glu Leu Arg Asp Thr Ile Tyr Leu Ala
                705                 710                 715

TCC CAG TTG GTA GAT CCT GCG TCA GAC GAA TTT GTA AAG TAT TAT CCA         2630
Ser Gln Leu Val Asp Pro Ala Ser Asp Glu Phe Val Lys Tyr Tyr Pro
                720                 725                 730

GAC TAC TTC AGA GAT CCG CAC ACG TAC GTG TAC TTG TTT CGT TTC AGA         2678
Asp Tyr Phe Arg Asp Pro His Thr Tyr Val Tyr Leu Phe Arg Phe Arg
        735                 740                 745

GGT CTG GGT GAT TTC GTG TTA TTA GAC TTG CAG ATT GTA CCA TTG CTA         2726
Gly Leu Gly Asp Phe Val Leu Leu Asp Leu Gln Ile Val Pro Leu Leu
        750                 755                 760

AAT TTG GCC ACT GTA CGT ATA GCC AAC ATC CAA AAC GGT CCC CAC TCG         2774
Asn Leu Ala Thr Val Arg Ile Ala Asn Ile Gln Asn Gly Pro His Ser
765                 770                 775                 780

TAC TTC GAT ACT TTG TAT TTT AAA GTG GAG TTG CGC GAC ACA AAC GGT         2822
Tyr Phe Asp Thr Leu Tyr Phe Lys Val Glu Leu Arg Asp Thr Asn Gly
                785                 790                 795

GCG ATT GTG TTT TCG TAT TCG CGC CGT GGC AAC GAG CCG ATG ACA CCC         2870
Ala Ile Val Phe Ser Tyr Ser Arg Arg Gly Asn Glu Pro Met Thr Pro
                800                 805                 810

GAA CAC CAT AAA TTT GAA GTG TAC AGT GGT TAC ACC GTA GAA TTG TTC         2918
Glu His His Lys Phe Glu Val Tyr Ser Gly Tyr Thr Val Glu Leu Phe
        815                 820                 825

ATG CGG GAA CCC GGT AAT CGA TTA CAA TTG ATT GTG AAC AAA ATG CTT         2966
Met Arg Glu Pro Gly Asn Arg Leu Gln Leu Ile Val Asn Lys Met Leu
        830                 835                 840

GAC ACA GCG TTG CCG TCT ACT CAA AAC ATT TTC GCT CGC ATC ACC GAC         3014
Asp Thr Ala Leu Pro Ser Thr Gln Asn Ile Phe Ala Arg Ile Thr Asp
845                 850                 855                 860

ACT CAA TTA GTG GTG GGG GAT ACG AGC ATT GAA GAT AAC CTT GTA ACG         3062
Thr Gln Leu Val Val Gly Asp Thr Ser Ile Glu Asp Asn Leu Val Thr
                865                 870                 875
```

| | | | | | | | | | | | | | | |
|---|---|---|---|---|---|---|---|---|---|---|---|---|---|---|
| AGT | ATT | AAT | GTA | GAT | TGT | GGC | GAC | GAC | GAC | AAC | CAA | AAG | ATA | AGA | GTT | 3110
| Ser | Ile | Asn | Val | Asp | Cys | Gly | Asp | Asp | Asp | Asn | Gln | Lys | Ile | Arg | Val |
| | | | 880 | | | | | 885 | | | | | 890 | | |

| | | | | | | | | |
|---|---|---|---|---|---|---|---|---|
| GTG | GAA | ACG | TTA | AAA | ATG | ATA | GCG | TTC | TAA | TAACGTTCAA | CAGTCAGTTA | 3160
| Val | Glu | Thr | Leu | Lys | Met | Ile | Ala | Phe |
| | | 895 | | | | | 900 | |

```
TCGACTGTCG CCGCGACGAC ATGACACTGG TGGGTGTAGT AGTTTGCGTG CTGTTGTTAT    3220

CGTCTGTAGA CGGTTATTCG TTTTATTCGT CGATTGAAGC CCTGCTTTTG AACGATCGCA    3280

CACAACTTTG CATAGGCGAC TGTTACGAAC GCAATGGCCA GCATTTGTGT GCCAGCACGT    3340

GGTCGGGATC AGAGTCTCGG TGCATAAGTG TTTTCAACAA GACCAAACAC TATCGTACGG    3400

AGACTAACGG AAAATGCATA AGTAACTGTG CCAACTTCAA CAACTACGCC CACGAATGGT    3460

GTGCCGTGTC CCGGTCGAAA TGGGGCCGTT GCAGCAGACG ACTGGCGCTC ACAGCGACAC    3520

GAACACACGC CACCCACAAC AAGTTCAAGA CATGTG                              3556
```

(2) INFORMATION FOR SEQ ID NO: 2:

(i) SEQUENCE CHARACTERISTICS:
           (A) LENGTH: 3572 basepairs
           (B) TYPE: Nucleic acid
           (C) STRANDEDNESS: Doublestranded
           (D) TOPOLOGY: Circular (ii) MOLECULE TYPE: Genomic DNA (iii) HYPOTHETICAL: No (iv) ANTI-SENSE: No (v) FRAGMENT TYPE: N/A (vi) ORIGINAL SOURCE:
           (A) ORGANISM: Pseudaletia unipuncta granulosis virus (vii) IMMEDIATE SOURCE:
           (A) LIBRARY: GENOMIC DNA
           (B) CLONE: EcoRI-I and subclones (viii) POSITION IN GENOME:
           (A) CHROMOSOME/SEGMENT: N/A
           (B) MAP POSITION: Unknown (ix) FEATURE:
           (A) NAME/KEY: Mature protein
           (B) LOCATION: 451 bp to 3155 bp
           (C) IDENTIFICATION METHOD: Experimentally
           (D) OTHER INFORMATION: Degrades special
                  Peritrophic Membrane proteins (ix) FEATURE:
           (A) NAME/KEY: Baculovirus very late
                promoter
           (B) LOCATION: 443 to 447 bp
           (C) IDENTIFICATION METHOD: Experimentally
           (D) OTHER INFORMATION: N/A (xi) SEQUENCE DESCRIPTION: SEQUENCE ID NO: 2:

```
ATGCATACAC ACCAGCTTCT GTTATAAATA CTGTATTAAA TTGCCAATTA GATGGAAGTT    60

GTGTATTTAT AAACGTTCGG TCCTGTATAT CTTGCCAATG ATTTGCGCCA TATTTGTTTT    120

ACATGATCTC GGATAGCTTT TTGAGGATTA GTGTATCCCA AAAATTGCGC TATACCATGT    180

CCGCGTACAT AAATTTATCA TTTTCCACTT CCACAATCCA AATTTCCGCA GAAACTCCTC    240

CAATGTTGCA CGATTTTTTT ACAAGAGTCA TTTTGCACGT TTACAAGAAA TTTATTACAA    300

GATTAGCTGC TTGTGATAAA GGTCTGCACG AGATGAGATT CAAATACGTA ATGAGAATTG    360

CGTGATTTGC ACGAGTTTAT ATAGCATAAT TTGCTAGGAA TGTCTGTTGG TTTGTGATGT    420
```

| | | | | | | | | | | | | | | | | | |
|---|---|---|---|---|---|---|---|---|---|---|---|---|---|---|---|---|---|
| TTAGGTGTTC | GCTGCATTAA | TTATAAGACT | | ATG<br>Met<br>1 | TCG<br>Ser | TAC<br>Tyr | AAA<br>Lys | GTG<br>Val<br>5 | ATT<br>Ile | GTA<br>Val | | | | | | | 471 |
| CCC<br>Pro | GCT<br>Ala | ACC<br>Thr<br>10 | GTG<br>Val | CTA<br>Leu | CCG<br>Pro | CCG<br>Pro | TGG<br>Trp | CTC<br>Leu<br>15 | AGA<br>Arg | GTC<br>Val | GGT<br>Gly | GAG<br>Glu | AAT<br>Asn<br>20 | TGG<br>Trp | ATA<br>Ile | TTC<br>Phe | 522 |
| GCA<br>Ala<br>25 | AGA<br>Arg | CAC<br>His | AGA<br>Arg | CGC<br>Arg | ACC<br>Thr<br>30 | GAG<br>Glu | GTG<br>Val | GGA<br>Gly | GTC<br>Val | GTT<br>Val<br>35 | CTA<br>Leu | CCG<br>Pro | GCG<br>Ala | AAC<br>Asn | ACG<br>Thr | AAA<br>Lys<br>40 | 573 |
| TTT<br>Phe | CGT<br>Arg | GTA<br>Val | CGA<br>Arg<br>45 | GCA<br>Ala | GAT<br>Asp | TTC<br>Phe | TCT<br>Ser | AGG<br>Arg<br>50 | GCG<br>Ala | GGC<br>Gly | TTC<br>Phe | ACC<br>Thr | CGA<br>Arg<br>55 | CCC<br>Pro | GTA<br>Val | ATA<br>Ile | 624 |
| GTG<br>Val | CGC<br>Arg<br>60 | CTC<br>Leu | TTG<br>Leu | AAC<br>Asn | AAC<br>Asn | AAC<br>Asn<br>65 | CGT<br>Arg | AAT<br>Asn | ACT<br>Thr | GAA<br>Glu | CGA<br>Arg<br>70 | GAA<br>Glu | ATC<br>Ile | AAC<br>Asn | TTG<br>Leu | AAC<br>Asn<br>75 | 675 |
| AAC<br>Asn | GAC<br>Asp | CAA<br>Gln | TGG<br>Trp | ATG<br>Met<br>80 | GAG<br>Glu | GTG<br>Val | GAG<br>Glu | CAT<br>His | GCG<br>Ala<br>85 | CAC<br>His | GAG<br>Glu | AGT<br>Ser | GTG<br>Val | CCG<br>Pro<br>90 | TTT<br>Phe | GTC<br>Val | 726 |
| GAT<br>Asp | TGG<br>Trp | CCG<br>Pro<br>95 | GTG<br>Val | GGC<br>Gly | GAA<br>Glu | AGG<br>Arg | AAC<br>Asn<br>100 | ATT<br>Ile | ATG<br>Met | GCC<br>Ala | GAA<br>Glu | GTG<br>Val<br>105 | TAT<br>Tyr | TTT<br>Phe | GAA<br>Glu | ATC<br>Ile | 777 |
| GAC<br>Asp<br>110 | GGA<br>Gly | CCA<br>Pro | CAC<br>His | ATA<br>Ile | CCG<br>Pro<br>115 | CTG<br>Leu | CCC<br>Pro | GTG<br>Val | TAC<br>Tyr | GTG<br>Val<br>120 | TTC<br>Phe | AAC<br>Asn | ACG<br>Thr | AGA<br>Arg | CCT<br>Pro<br>125 | GTC<br>Val | 828 |
| GAA<br>Glu | CAC<br>His | TTT<br>Phe | AAG<br>Lys<br>130 | AGC<br>Ser | GAG<br>Glu | TAT<br>Tyr | CGC<br>Arg | CAA<br>Gln<br>135 | AGT<br>Ser | TCG<br>Ser | TCT<br>Ser | GGC<br>Gly | TAC<br>Tyr<br>140 | TGC<br>Cys | TTT<br>Phe | CTA<br>Leu | 879 |
| TAT<br>Tyr | TTG<br>Leu<br>145 | GAC<br>Asp | CTG<br>Leu | GTC<br>Val | TGT<br>Cys | ATG<br>Met<br>150 | TTG<br>Leu | GTA<br>Val | CCG<br>Pro | CCC<br>Pro | GCT<br>Ala<br>155 | AGC<br>Ser | AAA<br>Lys | AAC<br>Asn | GCT<br>Ala | TTA<br>Leu<br>160 | 930 |
| TTG<br>Leu | GAC<br>Asp | GTG<br>Val | AAC<br>Asn | ATT<br>Ile<br>165 | TTC<br>Phe | GAG<br>Glu | CTT<br>Leu | CAT<br>His | CAA<br>Gln<br>170 | TTT<br>Phe | TAT<br>Tyr | AAC<br>Asn | GAA<br>Glu | ATC<br>Ile<br>175 | ATT<br>Ile | AAT<br>Asn | 981 |
| TAC<br>Tyr | TAT<br>Tyr | GAT<br>Asp<br>180 | GAC<br>Asp | CTG<br>Leu | TGC<br>Cys | GGC<br>Gly | TTG<br>Leu<br>185 | GTC<br>Val | GAG<br>Glu | GAT<br>Asp | CCA<br>Pro | TAC<br>Tyr<br>190 | GCA<br>Ala | GAC<br>Asp | ACT<br>Thr | GTC<br>Val | 1032 |
| GAT<br>Asp<br>195 | TCG<br>Ser | AAT<br>Asn | TTA<br>Leu | CCC<br>Pro | AAC<br>Asn<br>200 | AAG<br>Lys | GCT<br>Ala | GCT<br>Ala | TTC<br>Phe | GTG<br>Val<br>205 | AAA<br>Lys | GCT<br>Ala | GAT<br>Asp | GCT<br>Ala | GGC<br>Gly<br>210 | GGT<br>Gly | 1083 |
| CCG<br>Pro | GGT<br>Gly | GGT<br>Gly | GCG<br>Ala | TAT<br>Tyr<br>215 | TAT<br>Tyr | GGA<br>Gly | CCA<br>Pro | TTT<br>Phe | TGG<br>Trp<br>220 | ACG<br>Thr | GCA<br>Ala | CCG<br>Pro | GCG<br>Ala | AGC<br>Ser<br>225 | TCA<br>Ser | AAC<br>Asn | 1134 |
| CTT<br>Leu | GGT<br>Gly | GAT<br>Asp<br>230 | TAC<br>Tyr | CTC<br>Leu | AGA<br>Arg | ATA<br>Ile | TCG<br>Ser<br>235 | CCG<br>Pro | ACC<br>Thr | AAC<br>Asn | TGG<br>Trp | ATG<br>Met<br>240 | GTA<br>Val | ATT<br>Ile | CAC<br>His | GAG<br>Glu<br>245 | 1185 |
| CTG<br>Leu | GGT<br>Gly | CAT<br>His | GCA<br>Ala | TAC<br>Tyr<br>250 | GAT<br>Asp | TTT<br>Phe | GTG<br>Val | TTT<br>Phe | ACC<br>Thr<br>255 | GTC<br>Val | AAC<br>Asn | ACT<br>Thr | ATA<br>Ile | CTC<br>Leu<br>260 | ATT<br>Ile | GAA<br>Glu | 1236 |
| ATT<br>Ile | TGG<br>Trp | AAC<br>Asn<br>265 | AAC<br>Asn | TCT<br>Ser | TTA<br>Leu | TGC<br>Cys | GAT<br>Asp<br>270 | CGC<br>Arg | ATC<br>Ile | CAA<br>Gln | TAC<br>Tyr | AAG<br>Lys<br>275 | TGG<br>Trp | ATG<br>Met | AAC<br>Asn | AAA<br>Lys | 1287 |
| ACC<br>Thr<br>280 | AAA<br>Lys | AGA<br>Arg | CAA<br>Gln | CAA<br>Gln | CTG<br>Leu<br>285 | GCT<br>Ala | CGC<br>Arg | GTC<br>Val | TAT<br>Tyr | GAA<br>Glu<br>290 | AAT<br>Asn | AGA<br>Arg | CGA<br>Arg | CCG<br>Pro | CAG<br>Gln<br>295 | AAA<br>Lys | 1338 |
| GAG<br>Glu | GCG<br>Ala | ACC<br>Thr | ATT<br>Ile<br>300 | CAG<br>Gln | GCG<br>Ala | CTG<br>Leu | ATC<br>Ile | GAC<br>Asp<br>305 | AAT<br>Asn | AAC<br>Asn | AGC<br>Ser | CCG<br>Pro | TTC<br>Phe<br>310 | GAT<br>Asp | AAT<br>Asn | TGG<br>Trp | 1389 |
| GGC<br>Gly | TTT<br>Phe | TTT<br>Phe | GAG<br>Glu | AGG<br>Arg | CTG<br>Leu | ATA<br>Ile | ATA<br>Ile | TTC<br>Phe | ACG<br>Thr | TGG<br>Trp | CTG<br>Leu | TAC<br>Tyr | AAC<br>Asn | CCG<br>Pro | CAA<br>Gln | AGA<br>Arg | 1440 |

|           | 315 |     |     |     | 320 |     |     |     | 325 |     |     |     | 330 |     |     |     |      |
|-----------|-----|-----|-----|-----|-----|-----|-----|-----|-----|-----|-----|-----|-----|-----|-----|-----|------|
| GGA | CTA | GAC | ACA | TTG | CGT | AAC | ATC | AAC | CAT | TCG | TAC | AGG | GTG | CAC | GCC | ACC | 1491 |
| Gly | Leu | Asp | Thr | Leu | Arg | Asn | Ile | Asn | His | Ser | Tyr | Arg | Val | His | Ala | Thr | |
|     |     |     |     | 335 |     |     |     | 340 |     |     |     |     | 345 |     |     |     | |

```
                 315                           320                           325                          330
GGA CTA GAC ACA TTG CGT AAC ATC AAC CAT TCG TAC AGG GTG CAC GCC ACC   1491
Gly Leu Asp Thr Leu Arg Asn Ile Asn His Ser Tyr Arg Val His Ala Thr
                335                 340                     345

CGC AAC TCT TCT ATA CCG TAC CCG CAA ATA TGG TCA TGG CTA ACG ACT TCT   1542
Arg Asn Ser Ser Ile Pro Tyr Pro Gln Ile Trp Ser Trp Leu Thr Thr Ser
            350                 355                 360

GCT TAC GAC AAC TTT TGG TTA TAT TTT AAT TTG GTA GGC GTG TAC CCG GCA   1593
Ala Tyr Asp Asn Phe Trp Leu Tyr Phe Asn Leu Val Gly Val Tyr Pro Ala
365                     370                 375                 380

GAC TTT TAC GTA AAC GAA CAC AAC AAA GTT GTT CAT TTC AAT CTA CAC TTG   1644
Asp Phe Tyr Val Asn Glu His Asn Lys Val Val His Phe Asn Leu His Leu
            385                 390                     395

AGA GCT CTG GCG TTG GGG CAG AGT GTG CGT TAT CCC ATT AAA TAT ATA ATT   1695
Arg Ala Leu Ala Leu Gly Gln Ser Val Arg Tyr Pro Ile Lys Tyr Ile Ile
        400                 405                 410                 415

ACA GAC TTT GAT CTG GTG AGC AAA AAC TAC GAC ATT AAA CAG TAT TTA GAG   1746
Thr Asp Phe Asp Leu Val Ser Lys Asn Tyr Asp Ile Lys Gln Tyr Leu Glu
                    420                 425                 430

AGT AAT TTC GAT CTG GTT ATA CCA GAA GAA TTG CGG CAG ACC GAT TTG TTG   1797
Ser Asn Phe Asp Leu Val Ile Pro Glu Glu Leu Arg Gln Thr Asp Leu Leu
            435                 440                 445

GCG GAC GTG AGG GTG GTT TGT GTG ATT GAC GAT CCG TCG CAG ATT GTG GGC   1848
Ala Asp Val Arg Val Val Cys Val Ile Asp Asp Pro Ser Gln Ile Val Gly
450                     455                 460                 465

GAA CCG TTT AGC GTG TAC GAC GGG AAC GAG CGA GTG TTC GAG AGT ACG GTG   1899
Glu Pro Phe Ser Val Tyr Asp Gly Asn Glu Arg Val Phe Glu Ser Thr Val
            470                 475                 480

GCC ACG GAC GGA AAC ATG TAT CTG GTG GGC GTG GGT CCG GGA GTG TAC ACG   1950
Ala Thr Asp Gly Asn Met Tyr Leu Val Gly Val Gly Pro Gly Val Tyr Thr
485                     490                 495                 500

TTG CGT GCG CCA CGC GGC AAA AAC AAA CGC TAC AAA CTC CAT TTG GCA CAT   2001
Leu Arg Ala Pro Arg Gly Lys Asn Lys Arg Tyr Lys Leu His Leu Ala His
                505                 510                 515

TCG CCC AGA GAG CCC GTT CAT CCG GCC AAC GAC CAC ATG TAT CTG CTC GTG   2052
Ser Pro Arg Glu Pro Val His Pro Ala Asn Asp His Met Tyr Leu Leu Val
        520                 525                 530

ACG TAT CCC TAC TAC AAT CAA ACG TTG ACA TAC ACA CCG TAC GTA AAT TCT   2103
Thr Tyr Pro Tyr Tyr Asn Gln Thr Leu Thr Tyr Thr Pro Tyr Val Asn Ser
535                 540                 545                 550

GAC CTA GCC GTC GAC ATG GCT CAT TTG TTC GGC AGC AAC GAT CGT AGG TAT   2154
Asp Leu Ala Val Asp Met Ala His Leu Phe Gly Ser Asn Asp Arg Arg Tyr
            555                 560                 565

GTA GCC ACG ATA TAT TTC AAT CCA TTC GAA CAA ACA GTC ACC GTA CAT CTA   2205
Val Ala Thr Ile Tyr Phe Asn Pro Phe Glu Gln Thr Val Thr Val His Leu
570                 575                 580                     585

AAC AAT ATT CGT GCC GGT CGT GAA AAC AAC ACT ACC CTG TAC TTT GAA ATG   2256
Asn Asn Ile Arg Ala Gly Arg Glu Asn Asn Thr Thr Leu Tyr Phe Glu Met
            590                 595                 600

GTA ATT AGC AAC CCG TTC AAC GGG CAG AGC CAA ACT TTC ACT ATA CTC GAA   2307
Val Ile Ser Asn Pro Phe Asn Gly Gln Ser Gln Thr Phe Thr Ile Leu Glu
        605                 610                 615

GAC AAT CCC ACT TTA CGA CAA GGC TAC TAC AAA TTT GAC GTG GTC ACG TAC   2358
Asp Asn Pro Thr Leu Arg Gln Gly Tyr Tyr Lys Phe Asp Val Val Thr Tyr
620                 625                 630                     635

AGC TCC ATA AGG CTG AAT ATG AGC GTC GCG GGT CGG CTA TTA TTT GGC GAT   2409
Ser Ser Ile Arg Leu Asn Met Ser Val Ala Gly Arg Leu Leu Phe Gly Asp
            640                 645                 650

ACA TTT TTG CCG GAG GGT ACC ACC ACG CTG ACC ATG TTC CCA AAT CAA GTA   2460
```

-continued

| | | | | | | | | | | | | | | | | |
|---|---|---|---|---|---|---|---|---|---|---|---|---|---|---|---|---|
| Thr | Phe | Leu | Pro | Glu | Gly | Thr | Thr | Leu | Thr | Met | Phe | Pro | Asn | Gln | Val | |
| | 655 | | | | 660 | | | | 665 | | | | | 670 | | |
| CTT | GAG | CCC | AAT | TTG | TTT | CCA | GAC | GGT | TCC | GCC | TTG | AAT | AGG | ACA | TTG | GCA | 2511 |
| Leu | Glu | Pro | Asn | Leu | Phe | Pro | Asp | Gly | Ser | Ala | Leu | Asn | Arg | Thr | Leu | Ala |
| | | | | 675 | | | | 680 | | | | | 685 | | | |
| CGA | CTA | AGA | GAA | CAG | GCC | GCC | TTC | CTA | GAT | AAT | TAT | TCA | CAG | CTT | ATG | TAT | 2562 |
| Arg | Leu | Arg | Glu | Gln | Ala | Ala | Phe | Leu | Asp | Asn | Tyr | Ser | Gln | Leu | Met | Tyr |
| | | 690 | | | | | 695 | | | | | 700 | | | | |
| ATT | GAA | AAC | GAG | TTG | CGC | GAC | AGC | ATT | TAT | TTG | GCC | TCC | CAG | TTG | GTA | GAT | 2613 |
| Ile | Glu | Asn | Glu | Leu | Arg | Asp | Ser | Ile | Tyr | Leu | Ala | Ser | Gln | Leu | Val | Asp |
| 705 | | | | 710 | | | | 715 | | | | 720 | | | | |
| CCT | GCG | TCA | GAC | GAA | TTT | GTA | AAG | TAT | TAT | CCA | GAC | TAC | TTC | AGA | GAT | CCG | 2664 |
| Pro | Ala | Ser | Asp | Glu | Phe | Val | Lys | Tyr | Tyr | Pro | Asp | Tyr | Phe | Arg | Asp | Pro |
| | | | 725 | | | | | 730 | | | | 735 | | | | |
| CAC | ACG | TAC | GTG | TAC | TTG | TTT | CGT | TTC | AGA | GGT | CTG | GGT | GAT | TTT | GTG | TTA | 2715 |
| His | Thr | Tyr | Val | Tyr | Leu | Phe | Arg | Phe | Arg | Gly | Leu | Gly | Asp | Phe | Val | Leu |
| | 740 | | | | 745 | | | | 750 | | | | 755 | | | |
| TTA | GAC | TTG | CAG | ATT | GTA | CCA | TTG | CTA | AAT | TTG | GCA | ACT | GTA | CGT | ATA | GCT | 2766 |
| Leu | Asp | Leu | Gln | Ile | Val | Pro | Leu | Leu | Asn | Leu | Ala | Thr | Val | Arg | Ile | Ala |
| | | | 760 | | | | 765 | | | | 770 | | | | | |
| AAC | AAC | CAC | AAC | GGT | CCC | CAC | TCG | TAC | TTC | GAT | ACT | TTG | TAT | TTT | AAA | GTG | 2817 |
| Asn | Asn | His | Asn | Gly | Pro | His | Ser | Tyr | Phe | Asp | Thr | Leu | Tyr | Phe | Lys | Val |
| | | 775 | | | | 780 | | | | 785 | | | | | | |
| GAG | TTG | CGC | GAC | ACA | AAC | GGT | GCG | ATT | GTG | TTT | TCG | TAT | TCG | CGC | CGT | GGC | 2868 |
| Glu | Leu | Arg | Asp | Thr | Asn | Gly | Ala | Ile | Val | Phe | Ser | Tyr | Ser | Arg | Arg | Gly |
| 790 | | | | 795 | | | | 800 | | | | 805 | | | | |
| AAC | GAG | CCG | ATG | ACA | CCC | GAA | CAC | CAT | AAA | TTT | GAA | GTG | TAC | AGT | GGT | TAC | 2919 |
| Asn | Glu | Pro | Met | Thr | Pro | Glu | His | His | Lys | Phe | Glu | Val | Tyr | Ser | Gly | Tyr |
| | | | 810 | | | | 815 | | | | 820 | | | | | |
| ACC | GTA | GAA | TTG | TTC | ATG | CGG | GAA | CCC | GGT | AAT | CGA | TTA | CAA | TTG | ATT | GTG | 2970 |
| Thr | Val | Glu | Leu | Phe | Met | Arg | Glu | Pro | Gly | Asn | Arg | Leu | Gln | Leu | Ile | Val |
| | 825 | | | | 830 | | | | 835 | | | | 840 | | | |
| AAC | AAA | ATG | CTT | GAC | ACA | GCG | TTG | CCG | TCT | ACT | CAA | AAC | ATT | TTC | GCT | CGC | 3021 |
| Asn | Lys | Met | Leu | Asp | Thr | Ala | Leu | Pro | Ser | Thr | Gln | Asn | Ile | Phe | Ala | Arg |
| | | | 845 | | | | 850 | | | | 855 | | | | | |
| ATC | ACC | GAC | ACT | CAA | TTA | GTG | GTG | GGG | GAT | ACG | AGC | ATT | GAA | GAT | AAC | CTT | 3072 |
| Ile | Thr | Asp | Thr | Gln | Leu | Val | Val | Gly | Asp | Thr | Ser | Ile | Glu | Asp | Asn | Leu |
| | | 860 | | | | 865 | | | | 870 | | | | | | |
| GTA | ACG | AGT | ATT | AAT | GTA | GAT | TGT | GGC | GAC | GAC | GAC | AAC | CAA | AAG | ATA | AGA | 3123 |
| Val | Thr | Ser | Ile | Asn | Val | Asp | Cys | Gly | Asp | Asp | Asp | Asn | Gln | Lys | Ile | Arg |
| 875 | | | | 880 | | | | 885 | | | | 890 | | | | |
| GTT | GTG | GAA | ACG | TTA | AAA | ATG | ATA | GCG | TTC | TAA | TAACGTTCAA | | CAGTCAGTTA | | | | 3176 |
| Val | Val | Glu | Thr | Leu | Lys | Met | Ile | Ala | Phe | | | | | | | |
| | | 895 | | | | 900 | | | | | | | | | | |

| | | | | |
|---|---|---|---|---|
| TCGACTGTCG | CCGCGACGAC | ATGACACTGG | TGGGTGTAGT | AGTTTGCGTG | CTGTTGTTAT | 3236 |
| CGTCTGTACA | CGGTTATTCG | TTTTATTCGT | CGATTGAAGC | CCTGCTTTTG | AACGATCGCA | 3296 |
| CACAACTTTG | CATAGGCGAC | TGTTACGAAC | GCAATGGCCA | GCATTTGTGT | GCCAGCACGT | 3356 |
| GGTCGGGATC | AGAGTCTCGG | TGCATAAGTG | TTTTCAACAA | GACCAAACAC | TATCGTACGG | 3416 |
| AGACTAACGG | AAAATGCATA | AGTAACTGTG | CCAACTTCAA | CAACTACGCC | CACGAATGGT | 3476 |
| GTGCCGTGTC | CCGGTCGAAA | TGGGGCCGTT | GCAGCAGACG | ACTGGCGCTC | ACAGCGACAC | 3536 |
| GAACACACGC | CACCCACAAC | AAGTTCAAGA | CATGTG | | 3572 |